(12) United States Patent
Gabel et al.

(10) Patent No.: US 6,461,822 B2
(45) Date of Patent: *Oct. 8, 2002

(54) METHODS OF SCREENING COMPOUNDS FOR THEIR ABILITY TO INHIBIT THE PRODUCTION OF INFLAMMATORY CYTOKINES

(75) Inventors: Christopher A. Gabel, Ledyard, CT (US); Richard J. Griffiths, East Lyme, CT (US); James F. Eggler, Stonington, CT (US); Mark A. Dombroski, Waterford, CT (US); Kieran Geoghegan, Mystic, CT (US)

(73) Assignee: Pfizer Inc., New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/387,372

(22) Filed: Aug. 31, 1999

(65) Prior Publication Data

US 2002/0034764 A1 Mar. 21, 2002

Related U.S. Application Data

(60) Provisional application No. 60/098,448, filed on Aug. 31, 1998.

(51) Int. Cl.[7] .................. G01N 33/53; G01N 33/567; C07K 1/00; C07H 21/04; C07C 211/00
(52) U.S. Cl. .................. 435/7.2; 435/7.1; 530/350; 536/23.5; 564/305
(58) Field of Search .................. 435/7.1, 7.2; 530/350; 536/23.5; 564/305

(56) References Cited

U.S. PATENT DOCUMENTS

| 5,545,632 A |   | 8/1996 | Matsumori |
| 5,874,248 A | * | 2/1999 | Hillman et al. |
| 5,932,442 A | * | 8/1999 | Lal et al. |

FOREIGN PATENT DOCUMENTS

| WO | WO-95/31722 A1 | * | 11/1995 |
| WO | WO9938973 |   | 8/1999 |
| WO | WO9945910 |   | 9/1999 |

OTHER PUBLICATIONS

Valenzuela et al. J. Biol. CHem. 272(19):12575–12582, May 9, 1997.*
Okubo et al. Nat. Genet. 2(3):173–179, 1992.*
Kodym R., et al. Database GenEmbl. U90313. Direct Submission. Sep. 15, 1997.*
Lewis, R., *Nucleic Acids Research,* 14:(1), 567–570, 1986.
Sander, C., et al., *Proteins: Stuctures, Funcitons, and Genetics,* 9, 56–68, 1991.
Valenzuela, S., et al., *The Journal of Biological Chemstry,* 272:(19), 12575–12582, 1997.

* cited by examiner

*Primary Examiner*—Gary L. Kunz
*Assistant Examiner*—Robert S. Landsman
(74) *Attorney, Agent, or Firm*—Peter C. Richardson; Gregg C. Benson; Nicholas I. Slepchuk

(57) ABSTRACT

The present invention relates to the identification of diarylsulfonylurea binding proteins (DBPs) as therapeutic targets for agents that suppress the release of inflammatory mediators such as interleukin IL-1 and IL-1β.

24 Claims, 13 Drawing Sheets

FIG.4A

Amino Acid Sequence of DBP-32 (SEQUENCE ID NO 3):

```
         10          20          30          40          50
MAEEQPQVEL  FVKAGSDGAK  IGNCPFSQRL  FMVLWLKGVT  FNVTTVDTKR
         60          70          80          90         100
RTETVQKLCP  GGQLPFLLYG  TEVHTDTNKI  EEFLEAVLCP  PRYPKLAALN
        110         120         130         140         150
PESNTAGLDI  FAKFSAYIKN  SNPALNDNLE  KGLLKALKVL  DNYLTSPLPE
        160         170         180         190         200
EVDETSAEDE  GVSQRKFLDG  NELTLADCNL  LPKLHIVQVV  CKKYRGFTIP
        210         220         230         241
EAFRGVHRYL  SNAYAREEFA  STCPDDEEIE  LAYEQVAKAL  K
```

FIG. 4B cDNA sequence assignment for DBP-32 (SEQUENCE ID NO 1):

```
ATGGCTGAAGAACAACCGCAGTCGAATTGTTCGTGAAGGCTGGCAGTGATGGGGCCAAGATTGGCGAACT   70
GCCCATTCTCCCAGAGACTGTTCATGGTACTGTGGCTCAAGGGAGTCCACCTTCAATGTTACCACGTTGA   140
CACCAAAGGCGGACCGAGACAGTGCAGAGACACCACCAACAGAAGCTGTGCCAGGGCAGCTCCCATTCCTGCTCTGATGGC   210
ACTGAAGTGCACACAGACACCAACAGAAGCTGAGGAATTTCTGAGGCAGTGTGCCCTGTGCCCCAGGTACC   280
CCAAGCTGGCAGCTCTGAACCCTGAGTCCAACAGCTGGGCTGGACATATTTGCCAAATTTTCTGCCTA   350
CATCAAGAATTCAAACCCAGCACTCAATGACAATCTGGAGAAGGACTCCTGAAAGCCCTGAAGGTTTTA   420
GACAATTACTTAACATCCCCCTCCCAGAAGAAGTGATGAAACCAGTGCTGAAGATGAAGGTGTCTCTC   490
AGAGGAAGTTTTTGGATGGCAAGAGCTCACCCTGGCTGACTGCAACCTGTTGCCAAAGTTACACACATAGT   560
ACAGGTGGTGTAAGAAGTACCGGGGATTCACCATCCCCGAGGCCTTCACCTGTCCAGATGAGGAGATCGAGCTCGGTACTTG   630
AGCAATGCCTACGCCCGGAAGAATTCGCTTCCACCTGTCCAGATGAGGAGATCGAGCTCGCCTATG   700
AGCAAGTGGCAAAGGCCCTCAAA   723
```

FIG.5A

Amino acid sequence of DBP-31 (SEQUENCE ID NO 4):

```
         10          20          30          40          50
MSGESARSLG  KGSAPPGPVP  EGSIRIYSMR  FCPFAERTRL  VLKAKGIRHE
         60          70          80          90         100
VININLKNKP  EWFFKKNPFG  LVPVLENSQG  QLIYESAITC  EYLDEAYPGK
        110         120         130         140         150
KLLPDDPYEK  ACQKMILELF  SKVPSLVGSF  IRSQNKEDYA  GLKEEFRKEF
        160         170         180         190         200
TKLEEVLTNK  KTTFFGGNSI  SMIDYLIWPW  FERLEAMKLN  ECVDHTPKLK
        210         220         230         241
LWMAAMKEDP  TVSALLTSEK  DWQGFLELYL  QNSPEACDYG  L
```

FIG. 5B cDNA sequence of DBP-31 (SEQUENCE ID NO 2):

```
ATGTCCGGGGAGTCAGCCAGGAGCTTGGGGAAGGAAGCGCGCCCCCGGTCCCGGAGGGCTCGA      70
TCCGCATCTACACAGCATGAGGTTCTGCCCGTTTGCTGAGAGGACGCGTCTAGTCCTGAAGGCCAAGGGAAT  140
CAGGCATGAAGTCATCAATATCAACCTGAAAAATAAGCCTGAGTGGTTCTTTAAGAAAAATCCCTTTGT   210
CTGGTGCCAGTTCTGGAAAACAGTCAGGTCAGTCGATCTACGAGTCTGCCATCACCTGTGAGTACCTGG   280
ATGAAGCATACCCAGGAGAAGCTGTTGCCGGATGACCCCTATGAGAAAGCTTGCCAGAAGATGATCTT    350
AGAGTTGTTTCTAAGGTGCCATCCCTTGGTAGGAAGCTTTATTAGAAGCCAAAATAAAGAAGACTATGCT  420
GGCCTAAAAGAAGAATTTCGTAAAGAATTTACCAAGCTAGAGAGGTTCTGACTAATAAGACGGCTGGAAGCAAT 490
TCTTTGGTGGCAATTCTCTATCTCTATGATTGATTACCTCATCTGGCCCTGGTTTGAACGGCTGGAAGCAAT  560
GAAGTTAAATGAGTGTGTAGACCACACTCCAAAACTGAAACTGTGGATGGCAGCCATGAAGGAAGATCCC    630
ACAGTCTCAGCCCTGCTTACTAGTGAGAAAGACTGGCAAGGTTTCCTAGAGCTCTACTTACAGAACAGCC    700
CTGAGGCCCTGTGACTATGGGCTC                                                  723
```

FIG. 6

```
DBP-32  MAEEQPQVELFVKAGSDGAKIGN------CPFSQRLFMVLWLKGVT   40
DBP-31  MSGESARS--LGKGSAPPGPVPEGSIRIYSMRFCPFAERTRLVLKAKGIR  48

DBP-32  FNVTTVDYKRRTETVQKLCPGGQLPFLLYG-TEVHTDTNKIEEFLEAVLC   89
DBP-31  HEVININLKNKPEWFFKKNPFGLVPVLENSGQLIYESAITCEYLDEAYP   98

DBP-32  PPRYPKLAALNPESNTAGLDIFAKF---SAYIKNSNPALNDNLEKGLLK  135
DBP-31  GKKLLPDDPYEKACQKMILELFSKVPSLVGSFIRSQNKEDYAGLKEEFRK  148

DBP-32  ALKVLDNYLTSPLPE--EVDETSAEDEGVSQRKFLDGNELTLADC-NLLP  182
DBP-31  EFTKLEEVLTNKKTTFFGGNSISMIDYLIWPW-FBRLEAMKLNECVDHTP  197

DBP-32  KLHIVQVVCKKYRGFTIPEAFRGVHRYLSNAYAREEFASTCPDDEEIELA  232
DBP-31  KL-------KLWMAAMKED-PTVSALLTSEKDWQGFLELYLQNSPEACD  238

DBP-32  YEQVAKALK  241
DBP-31  YGL       241
```

FIG. 9

| Compound # | Name | % Inhibition at 1 μM |
|---|---|---|
| 1 | 1-(4-Chloro-2,6-diisopropyl-phenyl)-3-[2-fluoro-5-oxiranylbenzenesulfonyl]-urea | 71 |
| 2 | 1-(1,2,3,5,6,7-Hexahydro-s-indacen-4-yl)-3-[2-fluoro-5-oxiranylbenzenesulfonyl]-urea | 89 |
| 3 | 1-(4-Chloro-2,6-diisopropyl-phenyl)-3-[3-(1-hydroxy-ethyl)-benzenesulfonyl]-urea | 92 |
| 4 | 1-(1,2,3,5,6,7-Hexahydro-s-indacen-4-yl)-3-[4-(1-hydroxy-1-methylethyl)-furan-2-sulfonyl]-urea | 97 |
| 5 | 1-(1,2,3,5,6,7-Hexahydro-s-indacen-4-yl)-3-[5-fluoro-1H-indole-6-sulfonyl]-urea | 97 |
| 6 | 1-(2,6-diisopropyl-phenyl)-3-[5-fluoro-1H-indole-6-sulfonyl]-urea | 98 |
| 7 | 1-(4-Chloro-2,6-diisopropyl-phenyl)-3-[4-(1-hydroxy-1-ethyl)-thiophen-2-sulfonyl]-urea | 98 |
| 8 | 1-(1,2,3,5,6,7-Hexahydro-s-indacen-4-yl)-3-[4-(1-hydroxyimino-ethyl)-thiophene-2-sulfonyl]-urea | 98 |
| 9 | 1-(4-Chloro-2,6-diisopropyl-phenyl)-3-[5-acetyl-2-fluoro-benzenesulfonyl]-urea | 97 |
| 10 | 1-(4-Chloro-2,6-diisopropyl-phenyl)-3-[2-fluoro-5-(1-hydroxy-1-methylethyl)-benzenesulfonyl]-urea | 100 |

| Source of Conditioned Medium | Cytokine Level (ng/ml) | | |
|---|---|---|---|
| | IL-1ß | IL-6 | IL-1RA |
| Control | 31 | 26 | 128 |
| +1 µM Compound 3 | 0.98 | 19 | 137 |

SEQUENCE LISTING

<160> NUMBER OF SEQ ID NOS: 8

<210> SEQ ID NO 1
<211> LENGTH: 723
<212> TYPE: DNA
<213> ORGANISM: Homo sapiens

<400> SEQUENCE: 1

```
atggctgaag aacaaccgca ggtcgaattg ttcgtgaagg ctggcagtga tggggccaag      60
attgggaact gcccattctc ccagagactg ttcatggtac tgtggctcaa gggagtcacc     120
ttcaatgtta ccaccgttga caccaaaagg cggaccgaga cagtgcagaa gctgtgccca     180
```

-continued

```
gggggggcagc tcccattcct gctgtatggc actgaagtgc acacagacac caacaagatt      240
gaggaatttc tggaggcagt gctgtgccct cccaggtacc ccaagctggc agctctgaac      300
cctgagtcca acacagctgg gctggacata tttgccaaat ttctgcctca catcaagaat      360
tcaaacccag cactcaatga caatctggag aagggactcc tgaaagccct gaaggtttta      420
gacaattact aacatcccc cctcccagaa gaagtggatg aaaccagtgc tgaagatgaa       480
ggtgtctctc agaggaagtt tttggatggc aacgagctca ccctggctga ctgcaacctg      540
ttgccaaagt tacacatagt acaggtggtg tgtaagaagt accggggatt caccatcccc      600
gaggccttcc ggggagtgca tcggtacttg agcaatgcct acgcccggga agaattcgct      660
tccacctgtc cagatgatga ggagatcgag ctcgcctatg agcaagtggc aaaggccctc      720
aaa                                                                   723
```

<210> SEQ ID NO 2
<211> LENGTH: 723
<212> TYPE: DNA
<213> ORGANISM: Homo sapiens

<400> SEQUENCE: 2

```
atgtccgggg agtcagccag gagcttgggg aagggaagcg cgcccccggg gccggtcccg      60
gagggctcga tccgcatcta cagcatgagg ttctgcccgt ttgctgagag gacgcgtcta      120
gtcctgaagg ccaagggaat caggcatgaa gtcatcaata tcaacctgaa aaataagcct      180
gagtggttct ttaagaaaaa tccctttggt ctggtgccag ttctggaaaa cagtcagggt      240
cagctgatct acgagtctgc catcacctgt gagtacctgg atgaagcata cccagggaag      300
aagctgttgc cggatgaccc ctatgagaaa gcttgccaga gatgatcttt agagttgttt      360
tctaaggtgc catccttggt aggaagcttt attagaagcc aaaataaaga gactatgct       420 ggcctaaaag aagaatttcg taaagaattt accaagctag aggaggttct gactaataag      480
aagacgacct tctttggtgg caattctatc tctatgattg attacctcat ctggccctgg      540
tttgaacggc tggaagcaat gaagttaaat gagtgtgtag accacactcc aaaactgaaa      600
ctgtggatgg cagccatgaa ggaagatccc acagtctcag ccctgcttac tagtgagaaa      660
gactggcaag gtttcctaga gctctactta cagaacagcc tgaggcctg tgactatggg       720 ctc                                                                   723
```

<210> SEQ ID NO 3
<211> LENGTH: 241
<212> TYPE: PRT
<213> ORGANISM: Homo sapiens

<400> SEQUENCE: 3

```
Met Ala Glu Glu Gln Pro Gln Val Glu Leu Phe Val Lys Ala Gly Ser
  1               5                  10                  15

Asp Gly Ala Lys Ile Gly Asn Cys Pro Phe Ser Gln Arg Leu Phe Met
             20                  25                  30

Val Leu Trp Leu Lys Gly Val Thr Phe Asn Val Thr Thr Val Asp Thr
         35                  40                  45

Lys Arg Arg Thr Glu Thr Val Gln Lys Leu Cys Pro Gly Gly Gln Leu
     50                  55                  60

Pro Phe Leu Leu Tyr Gly Thr Glu Val His Thr Asp Thr Asn Lys Ile
 65                  70                  75                  80

Glu Glu Phe Leu Glu Ala Val Leu Cys Pro Pro Arg Tyr Pro Lys Leu
                 85                  90                  95
```

```
Ala Ala Leu Asn Pro Glu Ser Asn Thr Ala Gly Leu Asp Ile Phe Ala
            100                 105                 110

Lys Phe Ser Ala Tyr Ile Lys Asn Ser Asn Pro Ala Leu Asn Asp Asn
        115                 120                 125

Leu Glu Lys Gly Leu Leu Lys Ala Leu Lys Val Leu Asp Asn Tyr Leu
    130                 135                 140

Thr Ser Pro Leu Pro Glu Glu Val Asp Glu Thr Ser Ala Glu Asp Glu
145                 150                 155                 160

Gly Val Ser Gln Arg Lys Phe Leu Asp Gly Asn Glu Leu Thr Leu Ala
                165                 170                 175

Asp Cys Asn Leu Leu Pro Lys Leu His Ile Val Gln Val Val Cys Lys
            180                 185                 190

Lys Tyr Arg Gly Phe Thr Ile Pro Glu Ala Phe Arg Gly Val His Arg
        195                 200                 205

Tyr Leu Ser Asn Ala Tyr Ala Arg Glu Glu Phe Ala Ser Thr Cys Pro
    210                 215                 220

Asp Asp Glu Glu Ile Glu Leu Ala Tyr Glu Gln Val Ala Lys Ala Leu
225                 230                 235                 240

Lys

<210> SEQ ID NO 4
<211> LENGTH: 241
<212> TYPE: PRT
<213> ORGANISM: Homo sapiens

<400> SEQUENCE: 4

Met Ser Gly Glu Ser Ala Arg Ser Leu Gly Lys Gly Ser Ala Pro Pro
1               5                   10                  15

Gly Pro Val Pro Glu Gly Ser Ile Arg Ile Tyr Ser Met Arg Phe Cys
            20                  25                  30

Pro Phe Ala Glu Arg Thr Arg Leu Val Leu Lys Ala Lys Gly Ile Arg
        35                  40                  45

His Glu Val Ile Asn Ile Asn Leu Lys Asn Lys Pro Glu Trp Phe Phe
    50                  55                  60

Lys Lys Asn Pro Phe Gly Leu Val Pro Val Leu Glu Asn Ser Gln Gly
65                  70                  75                  80

Gln Leu Ile Tyr Glu Ser Ala Ile Thr Cys Glu Tyr Leu Asp Glu Ala
                85                  90                  95

Tyr Pro Gly Lys Lys Leu Leu Pro Asp Asp Pro Tyr Glu Lys Ala Cys
            100                 105                 110

Gln Lys Met Ile Leu Glu Leu Phe Ser Lys Val Pro Ser Leu Val Gly
        115                 120                 125

Ser Phe Ile Arg Ser Gln Asn Lys Glu Asp Tyr Ala Gly Leu Lys Glu
    130                 135                 140

Glu Phe Arg Lys Glu Phe Thr Lys Leu Glu Glu Val Leu Thr Asn Lys
145                 150                 155                 160

Lys Thr Thr Phe Phe Gly Gly Asn Ser Ile Ser Met Ile Asp Tyr Leu
                165                 170                 175

Ile Trp Pro Trp Phe Glu Arg Leu Glu Ala Met Lys Leu Asn Glu Cys
            180                 185                 190

Val Asp His Thr Pro Lys Leu Lys Leu Trp Met Ala Ala Met Lys Glu
        195                 200                 205

Asp Pro Thr Val Ser Ala Leu Leu Thr Ser Glu Lys Asp Trp Gln Gly
    210                 215                 220
```

```
Phe Leu Glu Leu Tyr Leu Gln Asn Ser Pro Glu Ala Cys Asp Tyr Gly
225                 230                 235                 240

Leu

<210> SEQ ID NO 5
<211> LENGTH: 26
<212> TYPE: DNA
<213> ORGANISM: Homo sapiens

<400> SEQUENCE: 5
aggatccacg atgtccgggg agtcag                                          26

<210> SEQ ID NO 6
<211> LENGTH: 24
<212> TYPE: DNA
<213> ORGANISM: Homo sapiens

<400> SEQUENCE: 6
cgaattcaga gcccatagtc acag                                            24

<210> SEQ ID NO 7
<211> LENGTH: 28
<212> TYPE: DNA
<213> ORGANISM: Homo sapiens

<400> SEQUENCE: 7
tacggatcca tggctgaaga acaaccgc                                        28

<210> SEQ ID NO 8
<211> LENGTH: 30
<212> TYPE: DNA
<213> ORGANISM: Homo sapiens

<400> SEQUENCE: 8
gtaggatcct tatttgaggg cctttgccac                                      30
```

METHODS OF SCREENING COMPOUNDS FOR THEIR ABILITY TO INHIBIT THE PRODUCTION OF INFLAMMATORY CYTOKINES

The present case claims priority from U.S. provisional patent application No. 60/098,448 filed Aug. 31, 1998.

BACKGROUND OF THE INVENTION

This invention relates to the identification of diarylsulfonylurea (DASU) binding proteins (DBPS) as novel therapeutic targets for suppressing the release of inflammatory mediators such as interleukin IL-1 and IL-1β.

Inflammatory diseases such as rheumatoid arthritis are characterized by an excessive production of cytokines that promote and/or maintain the inflammatory state. Prominent among them are IL-1 (both the α and β forms), tumor necrosis factor alpha (TNFα), and IL-18 (Dinarello, C. A. *Blood* 87:2095–2147 (1996); Aggarwal, B. B. and Natarajan, K. *Eur Cytokine Netw.* 7:93–124 (1996); Ushio, S. et al. *J. Immunol.* 156:4274–4279 (1996)). After release from producing cells, these cytokines bind to specific receptors on target cells to initiate cytokine signaling cascades. As a result of their importance in the disease process, therapeutic approaches aimed at regulating production and/or activity of these cytokines are desirable.

Most cytokines are secreted from cells via the constitutive secretory apparatus composed of the rough endoplasmic reticulum and Golgi apparatus, but IL-1 and IL-18 are exported by an untypical route (Rubartelli, A. et al. *EMBO J.* 9:1503–1510 (1990)). The need for a non-traditional export pathway is a consequence of the synthesis of IL-1 and IL-18 as polypeptides lacking signal sequences (Auron, P. E. et al. *Proc. Natl. Acad. Sci. USA* 81:7907–7911 (1984); March, C. J. et al. *Nature* 315:641–647 (1985); Ushio, S. et al. *J. Immunol.* 156:4274–4279 (1996)). This signal or leader sequence typically is found at the amino terminus of polypeptides which are destined to be released from the cell (von Heijne, G. *J. Membrane Biol.* 115:195–201 (1990)). A signal sequence serves as a molecular address to direct newly synthesized polypeptides into the endoplasmic reticulum. Because newly synthesized IL-1 (proIL-1) and IL-18 (proIL-18) lack this sequence, they accumulate within the cytoplasmic compartment of the producing cell. In addition to their co-localization, proIL-1β and proIL-18 also must be processed by the protease caspase I (Thornberry, N. A. et al. *Nature* 356:768–774 (1992); Ghayur, T. et al. *Nature* 360:619–623 (1997)); this cleavage generates biologically active, mature forms of the cytokines competent to bind to target cell receptors. ProIL-1α does not share this requirement for proteolytic activation (Moseley, B. et al. *J. Biol. Chem.* 262:2941–2944 (1987). Other polypeptides exported by similar non-traditional routes include: Mif-related protein (MRP) 8/14 (Rammes, A. et al. *J. Biol. Chem.* 272:9496–9502 (1997)), basic fibroblast growth factor (Abraham, J. A. *Science* 233: 545–548 (1986)), galectins (Cleves, A. E. et al. *J. Cell Biol.* 133:1017–1026 (1997)), a form of the IL-1 receptor antagonist (Haskill, S. et al. *Proc. Natl. Acad. Sci. USA* 88:3681–3685 (1991)), thioredoxin (Rubartelli, A. et al. *J. Biol. Chem.* 267:24161–24164 (1992)), and several virally-encoded polypeptides including VP22 and Tat (Ensoli, B. et al. *J. Virol.* 67:277–287 (1993)); Elliott, G. and O'Hare, P. *Cell* 88:223–233 (1997)).

Lipopolysaccharide (LPS)-treated monocytes and macrophages produce large quantities of proIL-1β, but the release of mature cytokine is inefficient in the absence of a secondary stimulus (Hogquist, K. A. et al. *J. Immunol.* 147:2181–2186 (1991)); Perregaux, D. et al. *J. Immunol.* 149:1294–1303 (1992)). Both proteolytic maturation of proIL-1β and the release of mature cytokine are enhanced by treating LPS-activated cells with any of a number of different stimuli including: extracellular ATP, cytolytic T-cells, high concentrations of LPS, ionophore-like molecules, toxins, hypotonic stress, and mechanical stress (Hogquist, K. A. et al. *Proc. Natl. Acad. Sci. USA* 88:8485–8489 (1991); Perregaux, D. and Gabel, C. A. *J. Biol. Chem.* 269:15195–15203 (1994); Walev, I. et al. *Eur. Mol. Biol. Org. J.* 14:1607–1614 (1995); Bhakdi, S. et al. *J. Clin. Invest.* 85:1746–1753 (1990); Chin, J. and Kostura, M. J. *J. Immunol.* 151:5574–5585 (1993)). Importantly, stimulus-coupled cytokine posttranslational processing is sensitive to pharmacological intervention. Thus, a variety of non-selective anion transport inhibitors such as ethacrynic acid and tenidap can block stimulus-coupled posttranslational processing of proIL-1β (Laliberte, R. et al. *J. Immunol.* 153:2168–2179 (1994); Perregaux, et al. *J. Immunol.* 157:57–64 (1996); Perregaux et al. *J. Immunol.* 160:2469–2477 (1998)). These agents are effective inhibitors of IL-1 posttranslational processing independent of the nature of the activating stimulus. Moreover, their inhibitory effect is manifested as a complete suppression in the externalization of both IL-1α and IL-1β.

A novel series of agents termed DASUs has been identified as potent inhibitors of stimulus-coupled posttranslational processing. These compounds are described and claimed in United States Provisional Application No. 1,086, 939 filed Jan. 27, 1997, the entire disclosure of which is hereby incorporated by reference. Because IL-1 and IL-18 are important mediators of inflammation and inhibitors of their function provide therapeutic relief in animal models of disease (Cominelli, F. et al. *J. Clin. Invest.* 86:972–980 (1990); Akeson, A. L. et al. *J. Biol. Chem.* 271:30517–30523 (1996); Caron, J. P. et al. *Arthritis Rheum.* 39:1535–1544 (1996); Okamura, H. et al. *Nature* 378:88–91 (1995); Rothwell, N. *J. Clin. Invest.* 100:2648–2652 (1997)), it is anticipated that agents that disrupt the process of stimulus-coupled posttranslational processing will be useful for the treatment in man and animals of disorders that are sustained by inflammatory mediators. These include rheumatoid arthritis, osteoarthritis, asthma, inflammatory bowel disease, ulcerative colitis, neurodegeneration, atherosclerosis, and psoriasis.

This invention relates to the identification of protein and DNA sequences corresponding to two DASU binding proteins (DBPs) that mediate the cytokine inhibitory activity of these agents. DBPs may be used to screen for structurally unique drugs that disrupt stimulus-coupled posttranslational processing. Compounds that bind to the DBPs also may be used as therapeutics in the treatment of inflammatory disorders.

The invention further relates to a pharmaceutical composition of a drug that binds to the DBPs.

The following abbreviations are used throughout this patent:

| | |
|---|---|
| ATP | adenosine triphosphate |
| DASU | diarylsulfonylurea |
| DBP | diarylsulfonylurea binding protein |
| EST | expressed sequence tag |
| GST | glutathione S-transferase |

-continued

| | |
|---|---|
| HPLC | high performance liquid chromatography |
| IL | Interleukin |
| kDa | kilodaltons |
| LC-MS | Liquid chromatograph-mass spectrometry |
| LPS | Lipopolysaccharide |
| PAGE | polyacrylamide gel electrophoresis |
| r | recombinant |
| RP-HPLC | reversed-phase high performance liquid chromatography |
| SDS | sodium dodecyl sulfate |
| TLC | thin layer chromatography |
| TNFα | tumor necrosis factor alpha |

SUMMARY OF INVENTION

In one embodiment, the present invention is directed to a method of screening for the ability of a compound to inhibit the production of an inflammatory cytokine comprising determining the ability of the compound to bind to a polypeptide coded for by the polynucleotide sequence of SEQUENCE ID NO: 1, or a polypeptide coded for by a polynucleotide sequence having 95% homology to SEQUENCE ID NO: 1.

Especially preferred is the method wherein the inflammatory cytokine is interleukin 1.

In another embodiment, the present invention is directed to method of treatment of a mammal having a disease condition characterized by an inflammatory component comprising administering to a mammal in need of such treatment a compound, or a pharmaceutically acceptable salt, ester, or prodrug of said compound, capable of binding to a polypeptide coded for by the polynucleotide sequence of SEQUENCE ID NO: 1, or a polypeptide coded for by a polynucleotide sequence having 95% homology to SEQUENCE ID NO: 1.

In yet another embodiment, the present invention is directed to a pharmaceutical composition comprising a pharmaceutical carrier and a pharmaceutically active amount of a compound, or a pharmaceutically acceptable salt, ester, or prodrug of said compound, said compound capable of binding to the polypeptide coded for by the polynucleotide sequence of SEQUENCE ID: NO: 1, or a polypeptide coded for by a polynucleotide sequence having 95% homology to SEQUENCE ID NO:1.

In yet still another embodiment, the present invention is directed to a method of screening for the ability of a compound to inhibit the production of inflammatory cytokine comprising determining the ability of the compound to bind to a polypeptide coded for by the polynucleotide sequence of SEQUENCE ID NO: 2, or a polypeptide coded for by a polynucleotide sequence having 95% homology to SEQUENCE ID NO: 2.

Especially preferred is the method wherein the inflammatory cytokine is interleukin 1.

In another embodiment, the present invention is directed to a method of treatment of a mammal having a disease condition characterized by an inflammatory component comprising administering to a mammal in need of such treatment a compound, or a pharmaceutically acceptable salt, ester, or prodrug of said compound, capable of binding to a polypeptide coded for by the polynucleotide sequence of SEQUENCE ID NO: 2, or a polypeptide coded for by a polynucleotide sequence having 95% homology to SEQUENCE ID NO: 2.

In yet still another embodiment, the present invention is directed to a pharmaceutical composition comprising a pharmaceutical carrier and a pharmaceutically active amount of a compound, or a pharmaceutically acceptable salt ester, or prodrug of said compound, said compound capable of binding to the polypeptide coded for by the polynucleotide sequence of SEQUENCE ID: NO: 2, or a polypeptide coded for by a polynucleotide sequence of having 95% homology to SEQUENCE ID NO:2.

In yet still another embodiment, the present invention is directed to a method of screening for the ability of a compound to inhibit the production of an inflammatory cytokine comprising determining the ability of the compound to bind to a polypeptide having the amino acid sequence of SEQUENCE ID NO: 3, or a polypeptide having 95% homology to SEQUENCE ID NO: 3.

Especially preferred is the method wherein the inflammatory cytokine is interleukin 1.

In another embodiment, the present invention is directed to a method of treatment of a mammal having a disease condition characterized by an inflammatory component comprising administering to a mammal in need of such treatment a compound, or a pharmaceutically acceptable salt, ester or prodrug of said compound, capable of binding to a polypeptide having the amino acid sequence of SEQUENCE ID NO: 3, or a polypeptide having 95% homology to SEQUENCE ID NO: 3.

In still another embodiment, the present invention is directed to a pharmaceutical composition comprising a pharmaceutical carrier and a pharmaceutically active amount of a compound, or pharmaceutically acceptable salt, ester, or prodrug of said compound, said compound capable of binding to the polypeptide of SEQUENCE ID: NO: 3, or a polypeptide having 95% homology to SEQUENCE ID NO: 3.

In yet still another embodiment, the present invention is directed to a method of screening for the ability of a compound to inhibit the production of an inflammatory cytokine comprising determining the ability of the compound to bind to a polypeptide having the amino acid sequence of SEQUENCE ID NO: 4, or a polypeptide having 95% homology to SEQUENCE ID NO: 4.

Especially preferred is the method wherein the inflammatory cytokine is interleukin 1.

In another embodiment, the present invention is directed to a method of treatment of a mammal having a disease condition characterized by an inflammatory component comprising administering to a mammal in need of such treatment a compound, or a pharmaceutically acceptable salt, ester, or prodrug of said compound, capable of binding to a polypeptide having the amino acid sequence of SEQUENCE ID NO: 4, or a polypeptide having 95% homology to SEQUENCE ID NO: 4.

In still another embodiment the present invention is directed to a pharmaceutical composition comprising a pharmaceutical carrier and a pharmaceutically active amount of a compound, or a pharmaceutically acceptable salt, ester, or prodrug of said compound, said compound capable of binding to the polypeptide having the amino acid sequence of SEQUENCE ID: NO: 4, or a polypeptide having 95% homology to SEQUENCE ID NO:4.

In another embodiment, the present invention is directed to the compound 1-(4-Chloro-2,6-diisopropyl-phenyl)-3-[2-fluoro-5-oxiranylbenzenesulfonyl]-urea.

In another embodiment, the present invention is directed to the compound 1-(1,2,3,5,6,7-Hexahydro-s-indacen-4-yl)-3-[2-fluoro-5-oxiranylbenzenesulfonyl]-urea.

BRIEF DESCRIPTION OF DRAWINGS

FIGS. 4A and 4B illustrate A) the amino acid sequence for DBP-32 (SEQUENCE ID NO: 3). Underlined amino acid residues indicate those identified by Edman sequence analysis and/or mass spectrometry in the radio labeled THP-1 cell polypeptide. B) The cDNA sequence for DBP-32 (SEQUENCE ID NO. 1).

FIG. 5A illustrates A) the amino acid sequence for DBP-31 (SEQUENCE ID NO: 4). Underlined amino acid residues indicate the identified by Edman sequence analysis and/or mass spectrometry in the radio labeled THP-1 cell polypeptide. B) The cDNA sequence for DBP-31 (SEQUENCE ID NO. 2).

FIG. 6 illustrates the sequence similarities between DBP-31 and DBP-32. The two amino acid sequences were aligned by the Clustal technique. Bolded residues are those that are identical in the two sequences.

FIG. 9 compares a number of structurally related DASUs as inhibitors of ATP-induced IL-1β posttranslational processing. LPS-activated monocytes were treated with ATP in the presence of the indicated compound after which IL-1β released into the medium was measured by ELISA. The extent of inhibition (% Inhibition relative to non-treated controls) observed at a concentration of 1 μM for each individual DASU is indicated.

DETAILED DESCRIPTION OF INVENTION

The procedure by which the DNA and protein sequences corresponding to the DASU binding proteins were identified and the use of agents that bind to these proteins as inhibitors of stimulus-coupled posttranslational processing are described below.

Discovery of DBPs

Figure 1:
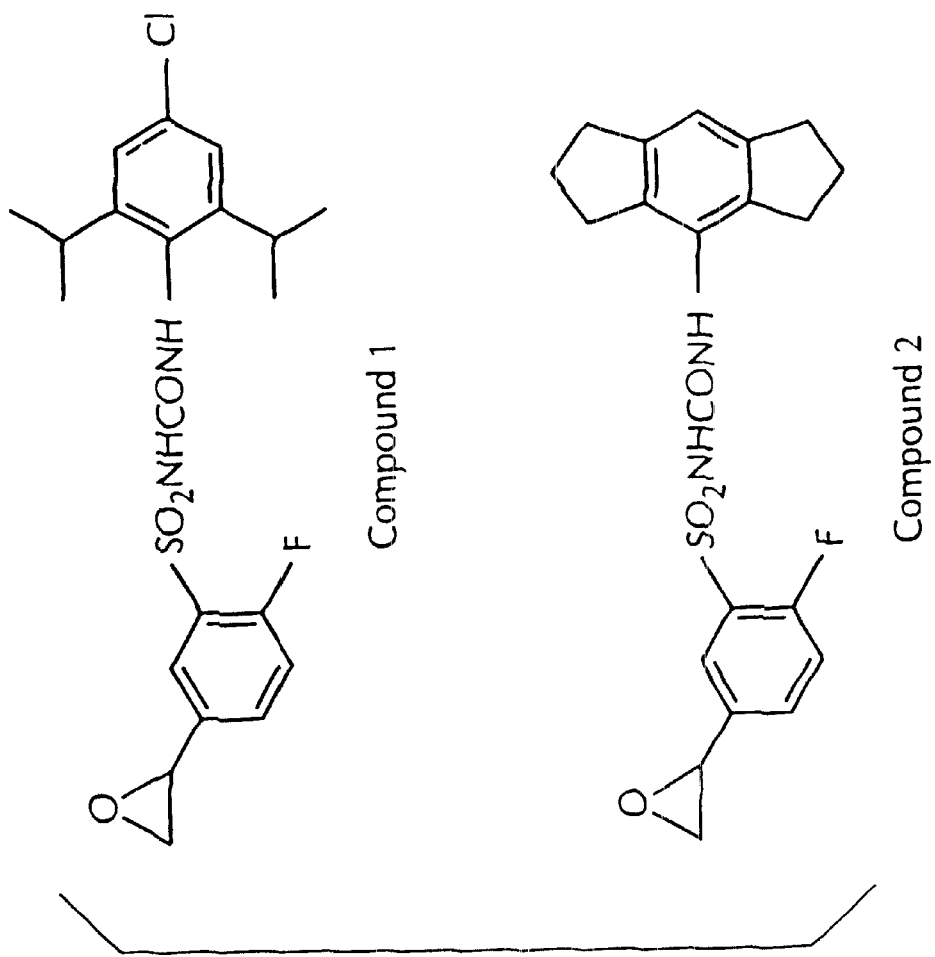
FIG. 1 illustrates the structure of two epoxide-containing DASUs employed to identify DASU binding proteins.
Figure 2A:
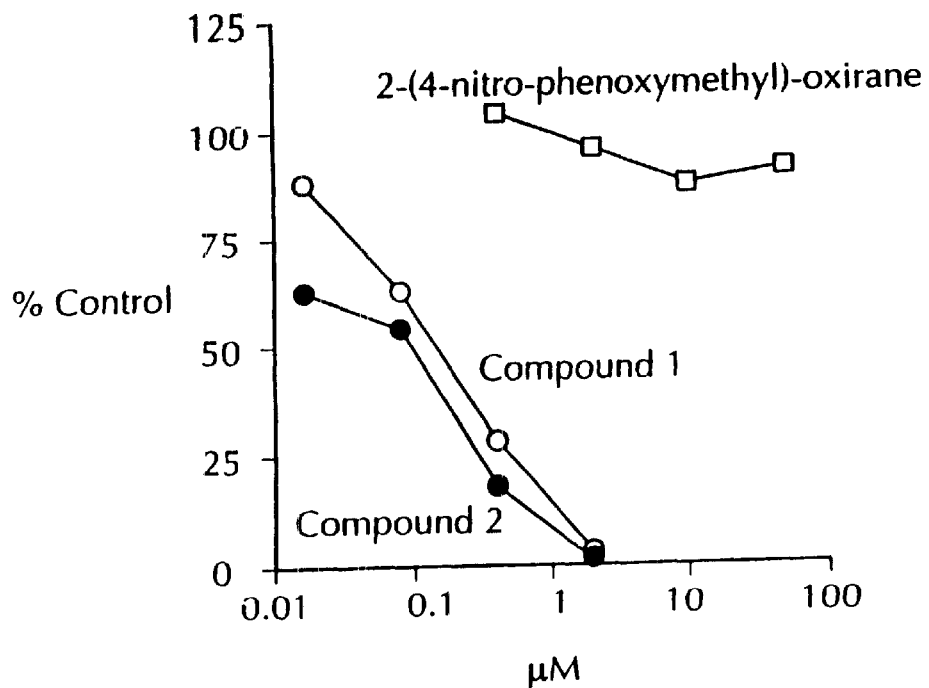
FIGS. 2A and 2B illustrate the utility of the epoxide-containing DASUs as inhibitors of ATP-stimulated IL-1β posttranslational processing. A) LPS-activated human monocytes were pretreated with the indicated concentration of test agent, then incubated with ATP (in the continued presence of the test agent). Media subsequently were harvested and their content of IL-1β was determined by ELISA; the amount of IL-1β produced at each test agent concentration is indicated as a percentage of that recovered in the absence of a test agent. B) LPS-activated human monocytes were treated for 60 min with the indicated concentration of Compound 2, after which the culture medium was replaced with fresh medium containing ATP but devoid of the compound. Media subsequently were harvested and their content of IL-1β was determined by ELISA. The amount of IL-1β detected is indicated as a percentage of that recovered from monocytes not pretreated with the DASU compound.
Figure 2B:
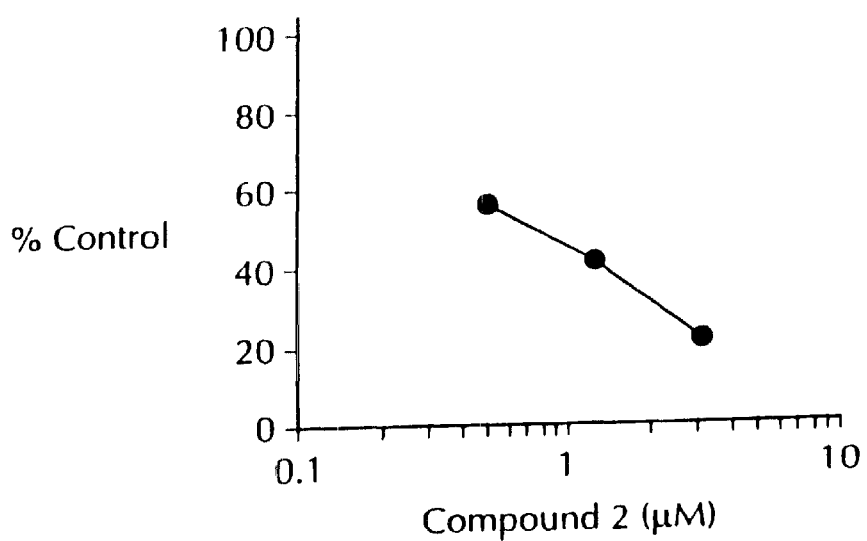

Based on their ability to inhibit stimulus-coupled IL-1β posttranslational processing, it was assumed that the DASUs must bind to one or more cellular proteins involved in the cytokine export pathway. To identify these, radiolabeled DASU analogs were synthesized containing an epoxide group that could react with functional groups on proteins to form covalent, irreversible adducts; the structures of two such agents, Compound 1 and Compound 2, are indicated in FIG. 1. Treatment of human monocytes continuously with either of these agents resulted in a dose-dependent inhibition in ATP-induced IL-1β production (FIG. 2A). In contrast, treatment with the structurally distinct epoxide-containing agent 2-(4-nitro-phenoxymethyl)-oxirane under the same experimental conditions did not inhibit IL-1 export (FIG. 2A). Therefore, structural features associated with the DASU agent, and not the epoxide per se, are necessary to achieve the cytokine inhibitory response. When monocytes were pretreated with Compound 2 for 60 min and then treated with ATP in its absence, IL-1β production remained suppressed (FIG. 2B). This irreversibility suggested that Compound 2 bound covalently to cellular proteins and that this interaction was responsible for the inhibition of cytokine posttranslational processing.

Figures 3A, 3B:
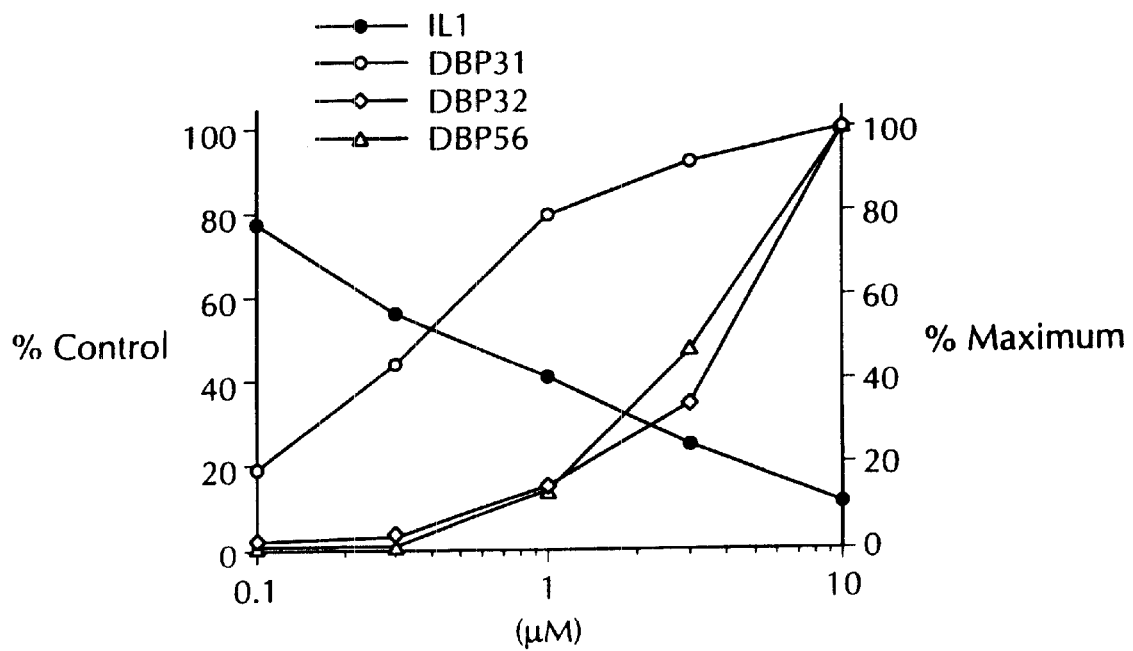
FIGS. 3A and 3B illustrate the utility of radiolabeled epoxide-containing DASUs as probes for identifying cellular binding proteins. A) Soluble polypeptides isolated from human monocytes that were treated with the indicated concentration of a [$^{14}$C]DASU Compound (Compound 1) or a different [$^{14}$C]DASU compound (Compound 2) (bottom) were fractionated by SDS PAGE, and radiolabeled polypeptides were detected by phosphorimager analysis. The apparent molecular masses of the three most highly labeled species are indicated on the right in kDa. B) Monocytes were pretreated with the indicated concentration of Compound 1 after which they were treated with ATP to promote IL-1β posttranslational processing. IL-1β released extracellularly (detected by ELISA) is indicated as a percentage (% Control) of that recovered from cells not pretreated with Compound 1. Soluble polypeptides recovered from cell extracts of the same ATP-treated monocytes were analyzed by SDS PAGE after which radiolabeled proteins were detected by phosphorimager analysis. The quantity of radioactivity associated with the 3 major radiolabeled polypeptides is expressed as a percentage of the maximum labeling (% Maximum) observed for each individual species as a function of the Compound 1 concentration.

To identify polypeptides that were covalently bound by the epoxide-containing DASUs, [$^{14}$C]labeled derivatives were synthesized, and cells treated with these radioactive probes were disrupted by nitrogen cavitation and separated into soluble and membrane fractions; these fractions subsequently were analyzed separately by SDS PAGE and autoradiography. No radiolabeled membrane-associated polypeptides were detected after treatment of LPS-activated monocytes with concentrations of the radiolabeled ligands ranging from 100 nM to 10 μm. In contrast, several radiolabeled polypeptides were detected in the soluble fraction of monocyte extracts derived from cells treated with Compound 1 or Compound 2 (FIG. 3). The three most prominent radiolabeled polypeptides possessed apparent masses of 31, 32, and 56 kDa. The extent of labeling of each polypeptide was dependent on the concentration of [$^{14}$C]labeled DASU. In a separate experiment, [$^{14}$C]Compound 1 treated cells were exposed to ATP to promote posttranslational processing of IL-1β prior to SDS gel analysis. The DASU-treated cells demonstrated a dose-dependent inhibition in IL-1 production (FIG. 3B). The concentration-dependence for labeling of the 31 kDa DBP showed an inverse correlation with the inhibition of IL-1β posttranslational processing (FIG. 3B). Labeling of the 32 and 56 kDa DASU binding proteins required higher concentrations of [$^{14}$C]Compound 1 to achieve maximal labeling than were required to inhibit the cytokine response and to maximally label DBP-31 (FIG. 3B).

Identification of DBPs

Human THP-1 cells treated with [$^{14}$C]Compound 1 yielded a similar set of 3 radiolabeled soluble polypeptides. Thus, [$^{14}$C]Compound 1 labeled THP-1 cells were employed as a starting source for isolation of the labeled polypeptides. A soluble fraction prepared from these cells was applied to an anion exchange column; the 31 kDa [$^{14}$C]-labeled polypeptide did not bind to the anion exchange resin. In contrast, the 32 and 56 kDa species bound and subsequently were eluted by a gradient of sodium chloride. At this stage of the purification, the radiolabeled 32 kDa polypeptide co-migrated with a discrete Coomassie Blue staining polypeptide on a one dimensional SDS polyacrylamide gel. Likewise, the 56 kDa polypeptide co-migrated with a discrete Coomassie Blue staining polypeptide on a two dimensional SDS polyacrylamide gel. These two polypeptides, therefore, were excised from the gels and subjected to sequence analysis (see below). The 31 kDa species, on the other hand, required additional purification. Material that ran through the anion exchange column was chromatographed on a Superose 12 HR 10/30 column; a single radiolabeled peak was eluted with an apparent $M_r$ of 30–40 kDa. Peak fractions were pooled, concentrated, and included polypeptides were fractionated by two-dimensional gel electrophoresis. A single radiolabeled polypeptide was detected on the two-dimensional gel map that corresponded to a distinct Coomassie Blue staining polypeptide. This polypeptide was excised and subjected to sequence analysis.

Peptides generated by separate tryptic digestion of the 31, 32, and 56 kDa gel-purified [$^{14}$C]Compound 1-labeled polypeptides were fractionated by reverse phase HPLC and analyzed by a combination of Edman degradation and mass spectrometry. Further analysis was conducted using LC-MS. Results from several experiments on each protein are combined in the following summaries.

DBP-56: Tryptic peptides were analyzed by LC-MS in an automated mode that furnished both mass measurements on the intact peptides and MS/MS data on the results of fragmenting them by collision. A computer based evaluation of the data provided a conclusive identification of DBP-56 as carboxylesterase. This protein demonstrates an apparent $M_r$ of 60 kDa on SDS PAGE (Munger, J. S. et al. *J. Biol. Chem.* 266:18832–18838 (1991)), consistent with the mass of DBP-56.

In order to assess whether DASUs inhibited carboxylesterase activity, an in vitro enzyme assay was established using porcine liver carboxylesterase and the artificial substrate p-nitrophenyl propionate (Krisch, K. *Biochem. Biophys. Acta* 122:265–280 (1966)). Co-incubation with 100 μM Compound 2 reduced the observed enzymatic activity by 67%, indicating that this DASU analog was a carboxylesterase inhibitor. However, analysis of other DASU analogs suggested that inhibition of carboxylesterase did not correlate with the ability of these compounds to inhibit IL-1β production by human monocytes. Thus, the interaction of the epoxide-containing DASUs with carboxylesterase is not considered relevant to their effect on cytokine posttranslational processing. Rather, the capacity of carboxylesterase to bind the epoxide-containing agents may reflect its role in metabolizing xenobiotics (Munger, J. S. et al. ibid).

DBP-32: N-Terminal sequence analysis of intact DBP-32 indicated that the protein was blocked, although subsequent CNBr cleavage of the sample allowed a short segment of internal sequence to be determined (see below). Tryptic digests of gel-purified DBP-32 were fractionated by HPLC and peaks at 220 nm were collected and subjected to sequence analysis. Resulting sequences matched theoretical tryptic peptides derived from a protein reported soon afterwards to be a chloride channel associated with intracellular membranes (accession #U93205; Valenzuela, S. M. et al. *J. Biol. Chem.* 272:12575–12582 (1997)). FIG. 4 indicates the amino acid sequence of this protein as predicted from the cDNA (FIG. 4B); peptide sections identified by protein sequencing of DBP-32 are indicated by underlying. LC-MS analysis of tryptic digests of DBP-32 gave further confirmatory coverage of the sequence. The results of sequencing the CNBr-cleaved protein indicated that the initiator methionine encoded by the cDNA is removed posttranslationally in the mature protein but the nature of the modified N-terminus is not yet known. The predicted amino acid sequence of this polypeptide corresponds to a 26.9 kDa polypeptide possessing a pI of 4.8. This polypeptide shows sequence homology to a 64 kDa chloride channel isolated from bovine epithelial cells and a 31 kDa chloride channel found in rat brain (Landry, D. et al. *J. Biol. Chem.* 268:14948–14955 (1993); Duncan, R. R. et al. *J. Biol. Chem.* 272:23880–23886 (1997)). Edman sequencing indicated that the amino acid residue corresponding to glutamic acid[63] in the U93205 sequence was actually glutamine in the THP-1 cell polypeptide; whether this difference represents a true polymorphism, a DNA sequencing error, or the result of a posttranslational modification is unknown.

DBP-31: N-Terminal sequence analysis of intact DBP-31 indicated that this protein was also blocked. Following tryptic digestion of gel-purified DBP-31 and HPLC fractionation of the digest, a number of peak fractions were subjected to automated Edman sequencing and MALDI-TOF MS. Several peptide sequences were obtained that matched predicted tryptic peptides encoded by a deposited human cDNA (accession #U90313; FIG. 5).

Two tryptic peptides from the same digest were not encompassed by the sequence given in the U90313 database entry as first deposited (dated Feb. 20, 1997) but matched DNA sequences located just upstream of the U90313 sequence and contiguous with it in expressed sequence tags (e.g. H81444 and N46067). This indicated that the true N-terminus of DBP-31 was upstream of that suggested in U90313 as originally deposited. Careful sequence analysis of clone N46067 yielded an open reading frame encoding the entire sequence predicted by U90313 but with a 29-residue amino terminal extension. This extension included the two peptides unaccounted for in U90313, one of which, (IYSMR) included the three C-terminal residues of the extension and the two N-terminal residues of the incomplete sequence U90313. The Mr predicted for this human polypeptide is 27,568 Da with a pI of 6.4.

Following our personal communication to a co-depositor of database entry #U90313 (Dr. M. D. Story) of our discovery that the deposited sequence was incomplete, the entry has now been updated to reflect the complete sequence.

Alignment of the DBP-31 and DBP-32 protein sequences indicates that these two proteins share sequence similarities (FIG. 6). Throughout their entire sequence, a 19% absolute identity is observed; a region near the amino terminus (residues 24–38 of DBP-32 and 32–46 of DBP-31) is particularly well conserved (FIG. 6). Thus, DBP-31 and DBP-32 appear to be members of the same protein family or superfamily.

Cloning and Expression of DBP-31/32

Figure 7A:
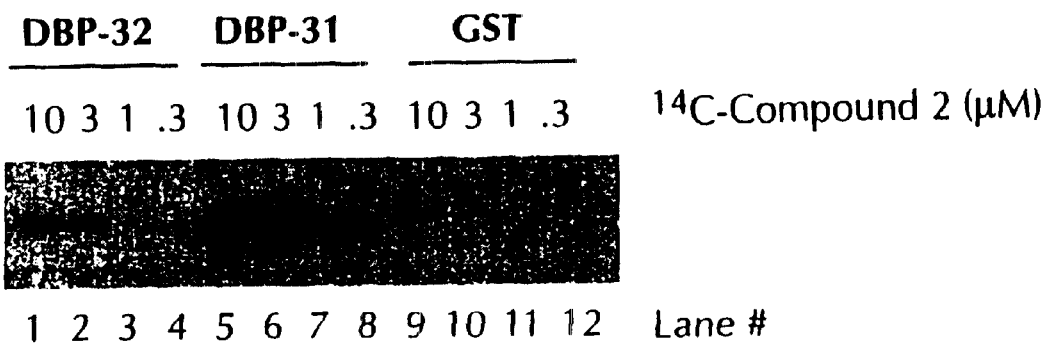
FIGS. 7A and 7B illustrate that recombinant DBPs retain the ability to bind Compound 2. A) Samples of rDBP-32, rDBP-31, or glutathione S-transferase (GST) were incubated with the indicated concentration of Compound 2 after which they were subjected to SDS PAGE and the dried gel was analyzed using a phosphorimager. B) rDBP-31 was incubated with 500 nM Compound 2 in the absence or presence of a non-epoxide containing DASU (Compound 4); the molar ratio of Compound 4 to Compound 2 is indicated. The samples were separated by SDS PAGE followed by phosphorimager analysis; each condition was performed in duplicate.
Figure 7B:
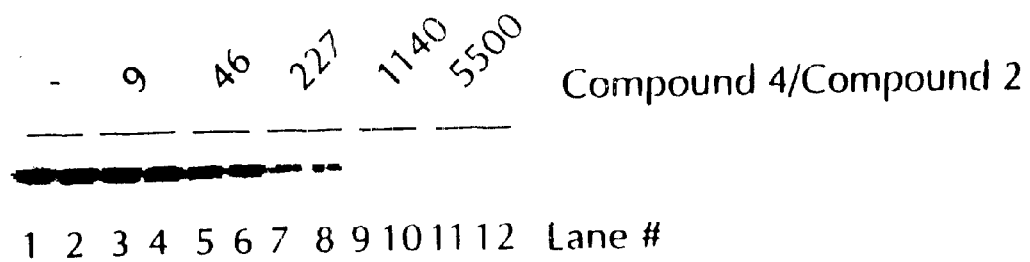

Separate bacterial expression vectors encoding bacterial glutathione S-transferase (GST) as a fusion partner of DBP-31 and DBP-32 were engineered and employed to transform bacteria. In the presence of an appropriate inducer, these bacteria produced large quantities of the fusion polypeptides. The recombinant (r) polypeptides were isolated from soluble cell extracts by affinity chromatography on Glutathione-Sepharose. Isolated fusion proteins subsequently were cleaved with thrombin to yield full-length rDBP-31 and rDBP-32 polypeptides and the mass of each isolated polypeptide was determined by electrospray mass spectrometry and agreed with the value predicted for the desired product.

rDBPs retained the ability of their cellular counterparts to interact with [$^{14}$C]Compound 2, demonstrating that these recombinant products were correctly folded and functional; hence they are valid proteins for use in screening experiments designed to discover new DBP-binidng drugs. Both rDBP-31 and rDBP-32 were labeled by [$^{14}$C]Compound 2 in a concentration dependent manner (FIG. 7A). In contrast, bacterial glutathione S-transferase was not labeled by [$^{14}$C] Compound 2 under identical conditions (FIG. 7A). As observed in the intact cells, lower DASU concentrations were required to label DBP-31 than were required to label rDBP-32 (FIG. 7A). Labeling of DBP-31 by [$^{14}$C] Compound 2 was inhibited by simultaneous incubation with Compound 4, a non-epoxide containing DASU analog (FIG. 7B). This type of competitive assay can be employed to identify agents that can compete with the radiolabeled DASUs for binding to the rDBPs, although it clearly is not the only form of assay that can be implemented for this purpose.

Figure 8A:
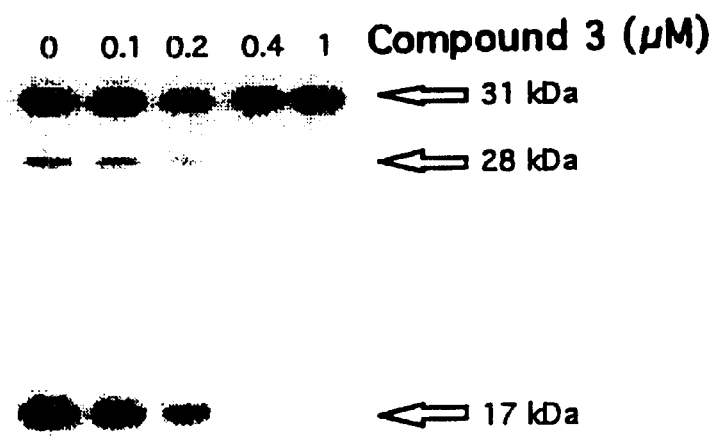
FIGS. 8A and 8B illustrate the utility of the non-epoxide containing DASU as an inhibitor of ATP-induced IL-1β posttranslational processing by human monocytes in vitro. A) LPS-activated/[$^{35}$S]methionine-labeled cells were pretreated with the indicated concentration of the non-epoxide containing DASU Compound 3 and then exposed to ATP in the continued presence of the DASU. Released IL-1β was recovered by immunoprecipitation and the immunoprecipitates were analyzed by SDS PAGE; an autoradiogram of the gel is indicated. Arrows on the right indicate the expected migration position of 31 kDa proIL-1β, 28 kDa alternative cleavage product, and 17 kDa mautre IL-1β. B) The amount of radioactivity recovered as 17 kDa IL-1β was determined and is indicated as a function of Compound 3 concentration.
Figure 8B:
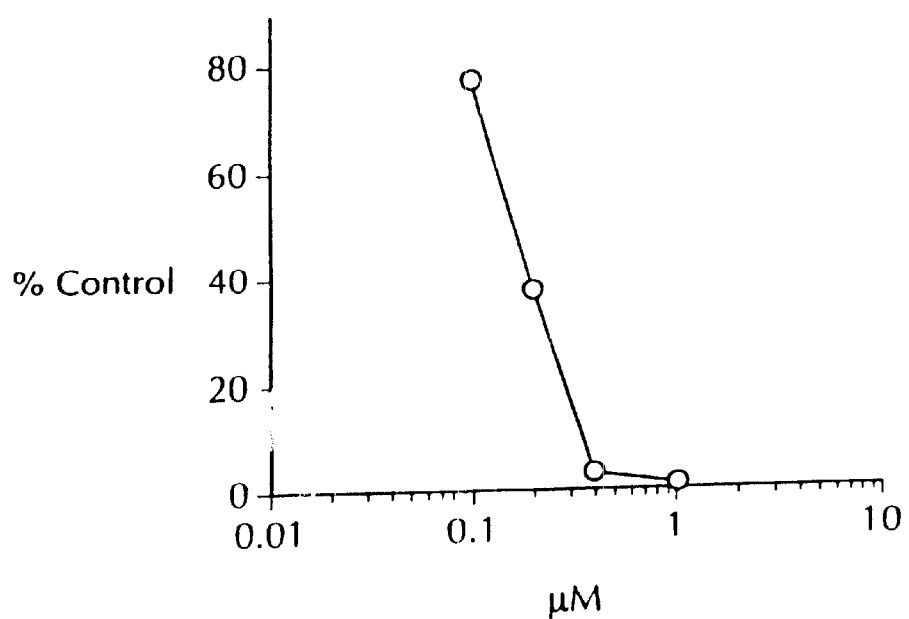

In vitro Demonstration of DASUs as Inhibitors of Stimulus-coupled IL-1 Posttranslational processing Human monocytes isolated from normal volunteers were activated with LPS and labeled with [$^{35}$S]methionine. These cells then were treated with ATP, which normally promotes proteolytic maturation and release of IL-1β, in the absence or presence of the DASU Compound 3. In the absence of Compound 3, ATP promoted release of the 17 kDa mature form of IL-1β (FIG. 8A). When Compound 3 was added to the medium and maintained throughout the period of ATP exposure, the amount of 17 kDa IL-1β released to the medium was reduced (FIG. 8A). The extent of inhibition was dependent on the concentration of the DASU added to the medium (FIG. 8B). FIG. 9 indicates that a number of structurally related DASUs can act to inhibit the cytokine response.

Figure 10A:
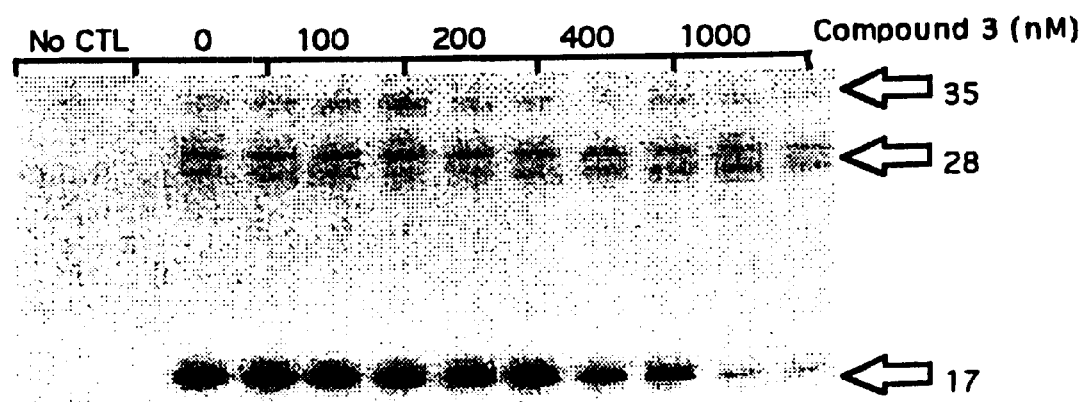
FIGS. 10A and 10B illustrate the utility of the non-epoxide containing DASU as an inhibitor of cytolytic T lymphocyte-mediated IL-1β posttranslational processing by murine peritoneal macrophages in vitro. A) LPS-activated/[$^{35}$S]methionine-labeled cells were pretreated with the indicated concentration of Compound 3 and then co-cultured with or without (No CTL) a preparation of allogeneic cytolytic T lymphocytes (in the continued presence of the DASU). After 4 hr of co-culture, released IL-1β was recovered by immunoprecipitation and the immunoprecipitates were analyzed by SDS PAGE; an autoradiogram of the immunoprecipitates is indicated. The expected migration positions of the 35 kDa, 28 kDa, and 17 kDa forms of murine IL-1β are indicated by arrows. B) The amount of radioactivity associated with the immunoprecipitated 17 kDa species was determined and is expressed as a percentage of that recovered in the absence of the DASU for each Compound 3 concentration.
Figure 10B:
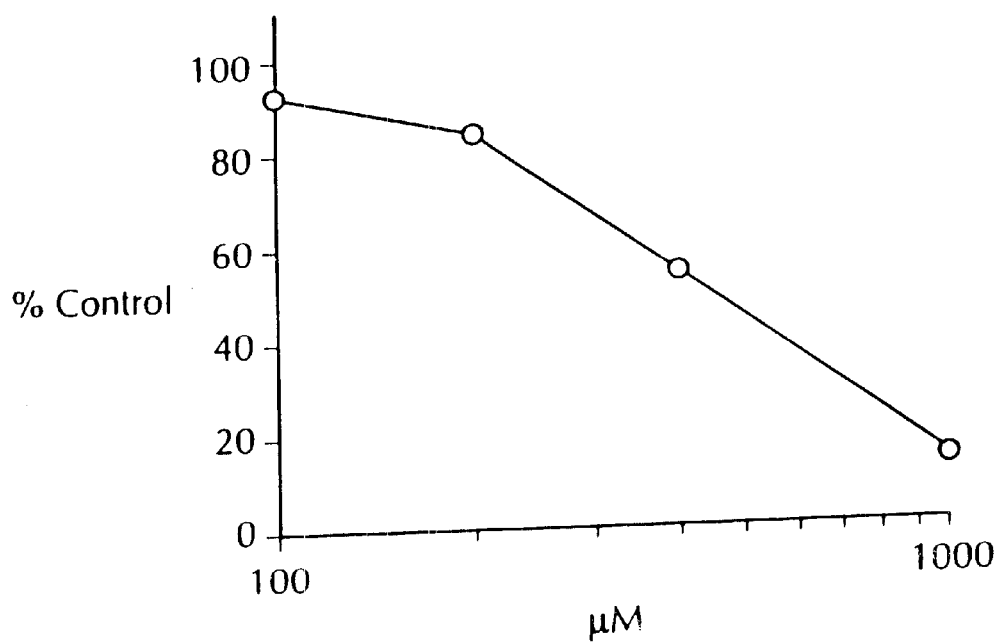

Inhibition of stimulus-coupled IL-1β posttranslational processing by DASUs is independent of the initiating stimulus, and is not limited to the ATP-induced process. An alternative method that has been employed in vitro to initiate efficient IL-1β posttranslational processing is to treat murine peritoneal macrophages with allogeneic cytolytic T lymphocytes (Hogquist et al. *Proc. Natl. Acad. Sci. USA* 88:8485–8489 (1991); Perregaux et al. *J. Immunol.* 157:57–64 (1996)). LPS-activated/$^{35}$S-methionine-labeled mouse peritoneal macrophages release mature 17 kDa IL-1β when treated with a preparation of allogeneic cytolytic T lymphocytes (FIG. 10A). In contrast, when incubated in the absence of the T lymphocytes the LPS-activated macrophages released little IL-1β (FIG. 10A). Inclusion of Compound 3 within the cytolytic T lymphocyte/macrophage co-cultures led to less producution of the extracellular mature cytokine species (FIG. 10A). The concentration of Compound 3 required to acheive 50% inhibition (IC$_{50}$) was estimated to be 425 nM (FIG. 10B). Therefore, DASUs may block a step in the cytokine export pathway that can be activated by a variety of exogenous signals. This common step is assumed to reflect the site of action of the DBPs.

Figures 11, 12:
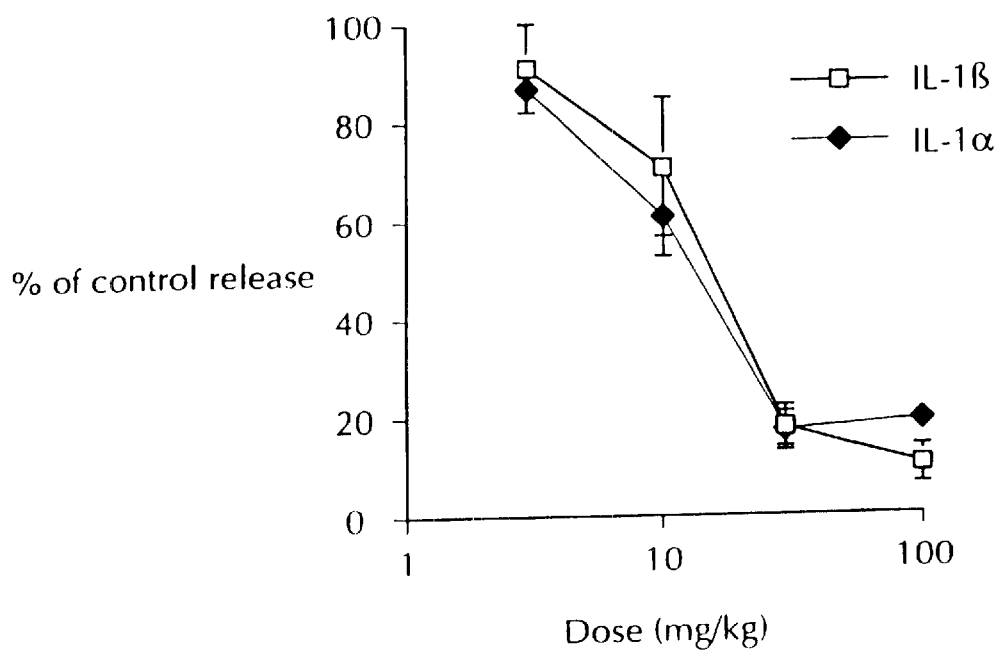
FIG. 11 illustrates the selectivity of Compound 3 as a cytokine inhibitor. Human monocytes were stimulated with LPS and treated with ATP in the absence or presence of 1 μM Compound 3. Media subsequently were harvested and assayed for their content of various cytokines using specific ELISA kits. Levels of IL-1β, IL-6, and IL-1 receptor antagonist (RA) produced in the presence and absence of Compound 3 are indicated.
FIG. 12 illustrates the utility of DASUs to inhibit the release of both IL-1α and IL-1β after oral administration to mice. Mouse peritoneal macrophages were stimulated in vivo with LPS and subsequently treated with ATP in animals dosed with varying amounts of Compound 3. Peritoneal lavage fluids were harvested and assayed for their content of IL-1 using specific ELISA kits. Levels of IL-1 α and IL-1β were measured and are indicated as a percentage of that released from peritoneal macrophages of vehicle treated mice.

In contrast, DASUs do not inhibit the release of cytokines that pass through the constitutive cellular secretory apparatus. This selectivity is readily demonstrated by comparing the cytokine content of growth medium conditioned by monocytes incubated in the absence or presence of Compound 3. Monocyte conditioned medium derived from cells activated with LPS/ATP contained high levels of IL-1β as well as high levels of two other cytokines, IL-1 receptor antagonist (RA) and IL-6, which are released via the constitutive secretory apparatus (FIG. 11). Conditioned medium harvested from monocytes maintained in the presence of Compound 3 contained less IL-1β (FIG. 11). In contrast, relative to their levels in control monocyte conditioned medium, media recovered from Compound 3-treated monocytes possessed comparable levels of IL-1RA and IL-6 (FIG. 11). Therefore, DASUs appear to selectively inhibit release of polypeptides whose export from monocytes/macrophages is dependent on a stimulus-induced export mechanism.

Demonstration that DASUs inhibit IL-1 production after administration to mice.

Injection of LPS into the peritoneal cavity of mice leads to the production of proIL-1β by resident peritoneal macrophages but formation and release of mature cytokine requires the subsequent injection of an inducer of posttranslational processing such as ATP into the peritoneal cavity (Griffiths, R. J. *J. Immunol.* 154:2821–2828 (1995)). To demonstrate that DASUs can prevent posttranslational processing of IL-1β in vivo, mice were dosed orally with Compound 3 and then subjected to the peritoneal cavity LPS/ATP assay; quantities of IL-1β recovered in the cell-free peritoneal lavage fluids subsequently were assessed by ELISA. Compound 3 dose-dependently inhibited production of IL-1β (FIG. 12). Likewise, this agent blocked the stimulus-induced release of IL-1α with similar effectiveness (FIG. 12). Oral administration of this DASU, therefore, represents a therapeutic approach for inhibiting production of IL-1.

A general utility of the DBPs is to allow screening for specific drugs that may represent improved therapeutics for use in inflammatory disorders. DBP-31 and DBP-32, or the DNA encoding their sequences which makes it possible for those skilled in the art to produce these proteins, can be used in vitro to establish assays for measuring the potency of compounds binding to these polypeptides.

Agents that bind to DBP-31/32 have utility as inhibitors of the production of cytokines such as IL-1 and IL-18 that are externalized by non-traditional stimulus-coupled post-translational processing. Administration of these agents to mammals thus constitutes a method to treat disorders characterized by the overproduction of inflammatory cytokines. These disorders include rheumatoid arthritis, osteoarthritis, inflammatory bowel disease, ulcerative colitis, neurodegeneration, stroke, sepsis, atherosclerosis, and asthma.

The compounds that bind to DBP's can also be used to produce pharmaceutical compositions.

MATERIALS AND METHODS

Synthesis of [$^{14}$C]-1-(4-Chloro-2,6-diisopropyl-phenyl)-3-[2-fluoro-5-oxiranylbenzenesulfonyl]-urea (1) and [$^{14}$C]-1-(1,2,3,5,6,7-Hexahydro-s-indacen-4-yl)-3-[2-fluoro-5-oxiranylbenzenesulfonyl]-urea (2)

[$^{14}$C]-labeled 1 and 2 were prepared by coupling 2-fluoro-5-oxiranyl-benzenesulfonamide VI with [$^{14}$C]4-isocyanato-1,2,3,5,6,7-hexahydro-5-indacene X and [$^{14}$C]-5-chloro-2-isocyanato-1,3-diisopropyl-benzene VIII respectively using sodium hydride in tetrahydrofuran. The labeled isocyanates were prepared by reaction of $^{14}$C-phosgene with either 4-chloro-2,6-diisopropyl-phenylamine VII or 1,2,3,5,6,7-hexahydro-5-indacen-4-ylamine IX and triethylamine in tetrahydrofuran or toluene as shown in Scheme 1.

The synthesis of 2-fluoro-5-oxiranyl-benzenesulfonamide VI is shown in Scheme 2. Dean-Stark distillation of a toluene solution of commercially available 1-(3-bromo-4-fluoro-phenyl)-ethanone I, ethylene glycol and a trace of p-toluenesulfonic acid gave 2-(3-bromo-4-fluoro-phenyl)-2-methyl-(1,3)dioxolane II. Successive treatment of II with n-butyllithium in tetra-hydrofuran at −78° C., sulfur dioxide, N-chlorosuccinimide in dichloromethane and aqueous ammonium hydroxide gave 2-fluoro-5-(2-methyl-[1,3]dioxolan-2-yl)-benzenesulfonamide III. Bromination of III with phenyltrimethylammonium tribromide in acetonitrile gave 5-(2-bromomethyl-[1,3]dioxolan-2-yl)-2-fluoro-benzenesulfonamide IV which was treated with aqueous hydrochloric acid in dioxane to give 5-bromoacetyl-2-fluoro-benzenesulfonamide V. Reduction of V with sodium borohydride in methanol, followed by treatment with dilute sodium hydroxide gave VI.

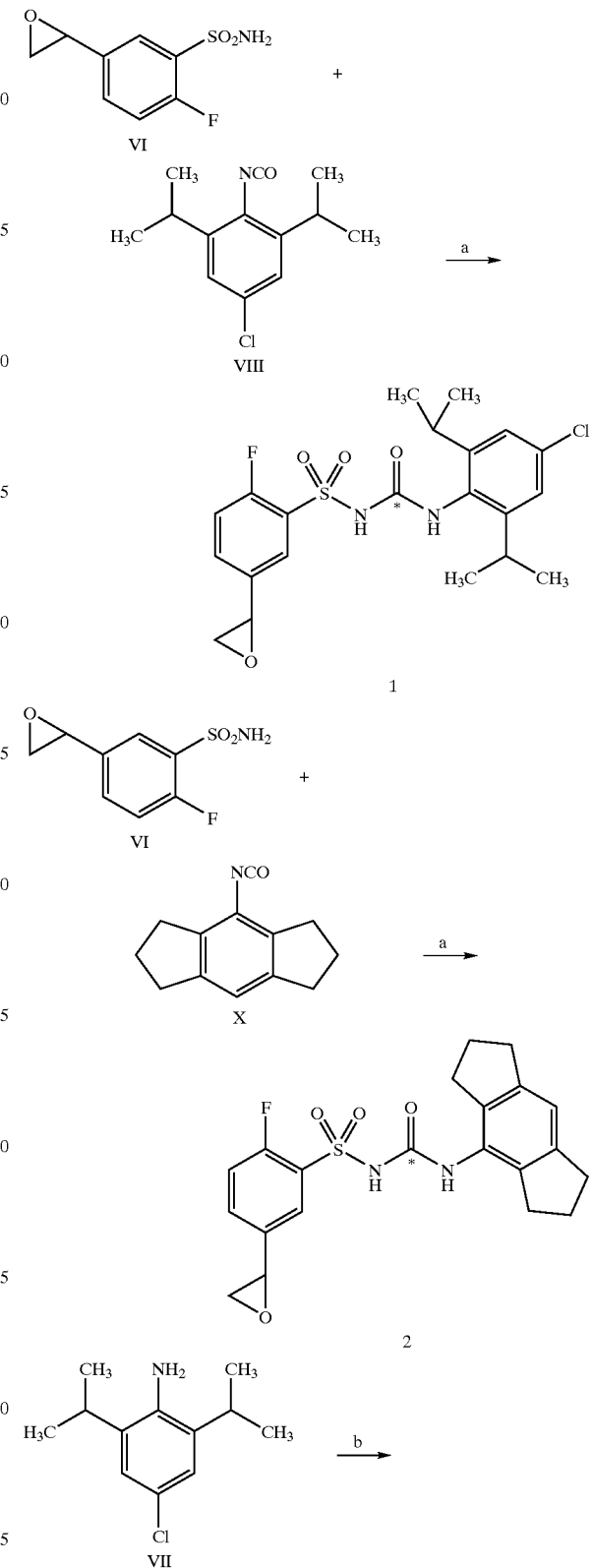

Scheme 1
Synthesis of Compounds 1 and 2

-continued

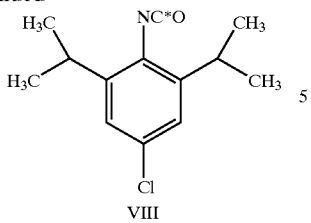

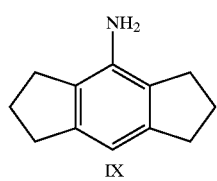

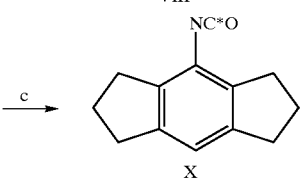

(a) NaH, tetrahydrofuran; (b) $^{14}$C-phosgene, triethylamine, toluene;
(c) $^{14}$C-phosgene, triethylamine, tetrahydrofuran. *Indicates the position of the $^{14}$C radiolabel.

-continued

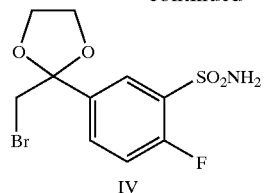

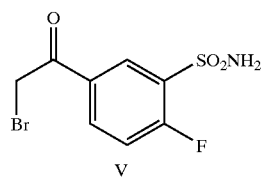

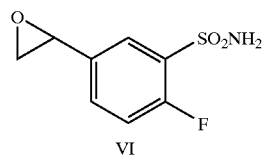

(a) TsOH, ethylene glycol, toluene; (b) BuLi, THF; (c) SO$_2$;
(d) NCS, methylene chloride; (e) NH$_4$OH; (f) Ph(CH$_3$)$_3$NBr$_3$, acetonitrile;
(g) HCl$_{aq}$, dioxane; (h) NaBH$_4$, methanol.

2-(3-Bromo-4-fluoro-phenyl)-2-methyl-(1,3)dioxolane II

A solution of 25 g (0.115 mole) of 1-(3-bromo-4-fluoro-phenyl)-ethanone I (Fluorochem), 20 mL (0.345 mole) of ethylene glycol and a trace of p-toluenesulfonic acid in 200 mL of toluene was heated at reflux for 12 hrs with Dean-Stark separation of water. The reaction was cooled to room temperature, washed with a dilute sodium bicarbonate solution, dried over Na$_2$SO$_4$ and the solvent was evaporated to give 30 g of 11(100%) as an oil. TLC:CH$_2$Cl$_2$ single spot material Rƒ 0.040. $^1$H-NMR (300 MHz DMSO-D$_6$) δ: (1.52, s, 3H), (3.67, m, 2H), (3.95, m, 2H), (7.34, m, 1H), (7.40, m, 1H), 7.63, m, 1H).

Scheme 2
Synthesis of VI

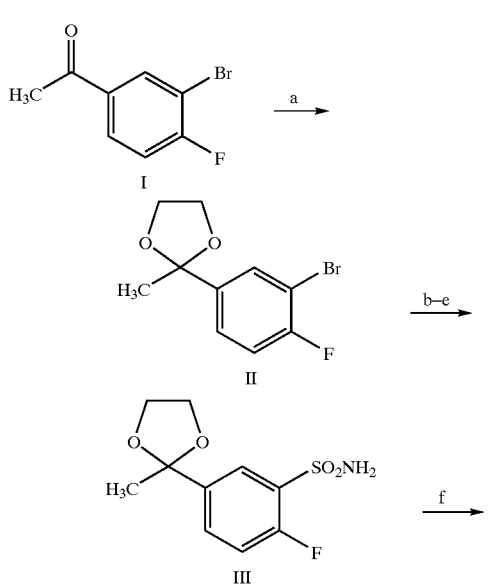

2-Fluoro-5(2-methyl-[1,3]dioxolan-2-yl)-benzenesulfonamide III n-BuLi [1.6 M in hexane, 50 mL (0.08 mole)] was added dropwise to a solution of 20.88 g (0.08 mole) of 2-(3-bromo-4-fluoro-phenyl)-2-methyl-(1,3)dioxolane II in 200 mL tetrahydrofuran at −78° C. After stirring for 2 hrs at −78° C., SO$_2$ was bubbled in for 15 min. The reaction was allowed to warm to room temperature and stirred overnight. A solution of 10.8 g (0.08 mole) of NCS in 150 mL of CH$_2$Cl$_2$ was added and the reaction stirred for 1 hr. The volatiles were evaporated in vacuo, and the brown residue was slurried with CH$_2$Cl$_2$ and filtered. The filtrate was treated with 200 mL of 30% NH$_4$OH and stirred for 3 hrs. The CH$_2$Cl$_2$ layer was separated, dried over Na$_2$SO$_4$ and evaporated. The residue was triturated with CH$_2$Cl$_2$ and filtered to give 8.1 g of III (77%); mp 149–150° C.TLC: CH$_2$Cl$_2$/MeOH::9/1 single-spot material Rƒ 0.5. $^1$H NMR (300 MHz, DMSO-D$_6$) δ: (1.60, s, 3H), (3.70, m, 2H), (4.05, m, 2H), (7.41, t, 1H), (7.71, broad s, 3H), (7.84, dd, 1H).

5-(2-bromomethyl-[1,3]dioxolan-2-yl)-2-fluoro-benzenesulfonamide IV

A solution of 8.4 g (0.0225 mole) of phenyltrimethylammonium tribromide in 20 mL of CH$_3$CN was added dropwise to a solution of 5.2 g (0.022 mole) 2-fluoro-5(2-methyl-[1,3]dioxolan-2-yl)-benzenesulfonamide III in 100 mL of CH$_3$CN. The reaction was stirred at room temperature for 1 hr. The solvent was evaporated in vacuo. The residue was dissolved in EtOAc, washed with water, dried over Na$_2$SO$_4$ and evaporated. The residue was purified by column chromatography on silica gel eluting with CH$_2$Cl$_2$/Et$_2$O::9/1 to give 4.6 g of IV (62%) as an oil. CH$_2$Cl$_2$/Et$_2$O::9/1 single-spot material Rƒ 0.30. $^1$H NMR (300 MHz CDCl$_3$) δ: (3.68, s, 2H), (3.80,m, 2H), (4.21, m, 2H), 5.15, broad s, 2H), (7.26, t, 1H), (7.75, m, 1H), 8.15, dd, 1H).

5-Bromoacetyl-2-fluoro-benzenesulfonamide V

A solution of 1.5 g (4.4 mmol) of 5-(2-bromomethyl-[1,3]dioxolan-2-yl)-2-fluoro-benzenesulfonamide IV in 50 mL of dioxane and 10 mL of 2N HCl was heated at reflux for 5 hrs then cooled to room temperature. The solvent was evaporated in vacuo and the residue was dissolved in EtOAc, washed with $H_2O$, and dried over $Na_2SO_4$. The residue was purified by column chromatography on silica gel eluting with EtOAc to give 900 mg of material which was recrystallized from MeOAc to give 700 mg V (54%); mp 153–158° C.TLC: $CH_2Cl_2/Et_2O$::7/3 single-spot material Rƒ 0.60.$^1$H NMR (300 MHz DMSO-D$_6$) δ: (5.20, s 2H), (7.63, t, 1H), (7.86, broad s, 2H), (8.32, m, 2H).

2-Fluoro-5-oxiranyl-benzenesulfonamide VI

A solution of 0.5 g (1.7 mmol) of 5-bromoacetyl-2-fluoro-benzenesulfonamide V in 20 mL MeOH was cooled to 0° C. NaBH$_4$ 26 mg (0.67 mmol) was added and the reaction was stirred at 0° C. for 15 min. 4 mL of 1N NaOH was added and the reaction was stirred at 0° C. for 4 hrs. The reaction was adjusted to pH 6 by addition of dilute HCl. The volatiles were evaporated and the residue dissolved in EtOAc, washed with $H_2O$, dried over $Na_2SO_4$ and evaporated. The product was purified by column chromatography on silica gel eluting with $CH_2Cl_2$/MeOH::9/1 to give 180 mg of VI (48%); mp 100–103° C.TLC:$CH_2Cl_2$/MeOH::9/1 single-spot material Rƒ 0.65.$^1$H-NMR (300 MHz DMSO-D$_6$) δ: (2.82, m, 1H), (3.14, m, 1H), (4.06, m, 1H), (7.40, t, 1H), (7.56, m, 1H), (7.66, m, 3H).

4-Chloro-2-isocyanato-1,3-diisopropyl-benzene VII (non-labeled)

To a solution of 8.9 g (0.042 mole) of 4-chloro-2,6-diisopropyl-phenylamine VII (which is prepared in quantitative yield by treatment of commercially available 2,6-diisopropylamine with N-chlorosuccinimide and N,N-dimethylformamide) and 4.66 g (0.046 mole) of triethylamine in 125 mL of tetrahydrofuran was added 23.8 mL (0.046 mole) of a 1.93 M solution of phosgene in toluene. The reaction was stirred at room temperature for 15 min, then at 70° C. for 15 min. The solvents were evaporated in vacuo. The residue was dissolved in hexane and purified on a plug of silica gel eluting with 10% $CH_2C_2$/hexane to give 9.45 g of non-labeled VIII (95%) as an oil.TLC:Hex/$CH_2Cl_2$::2/1 single spot material Rƒ 0.70.$^1$H-NMR (300 MHz CDCl$_3$) δ: (1.20, d, 12H), (3.19, septet, 2H), (7.06, s, 2H). (2.13, t, 4H), (2.85, m, 8H), (6.93, s, 1H).

4-Isocyanato-1,2,3,5,6,7-hexahydro-s-indacene X (non-labeled)

To a solution of 1.77 g (0.01 mole) of 1,2,3,5,6,7-hexahydro-s-indacen-4-ylamine IX (Vejdelek et al. *Coll. Czech Chem. Comm.* 42: 3094 (1977) and 1.11 g (0.011 mole) of triethylamine in 25 mL of tetrahydrofuran was added 5.7 mL (0.011 mole) of a 1.93 M solution of phosgene in toluene. The reaction was stirred at room temperature for 15 min and at 70° C. for 15 min. The solvents were evaporated in vacuo. The residue was dissolved in hexane and purified on a plug of silica gel eluting with 10% $CH_2Cl_2$/hexane to give 1.79 g of non-labeled X (90%); mp 40–41° C. TLC:Hex/$CH_2Cl_2$::2/1 single-spot material Rƒ 0.70.$^1$H-NMR (300 MHz CDCl$_3$) δ: (2.13, t, 4H), (2.85, m, 8H), (6.93, s, 1H).

1-(4-Chloro-2,6-diisopropyl-phenyl)-3-[2-fluoro-5-oxiranylbenzene-sulfonyl]-urea (1) (non-labeled)

Sodium hydride [60% dispersion in mineral oil, 23 mg (0.57 mmol)] was added to a solution of 113 mg (0.52 mmol) of 2-fluoro-5-oxiranyl-benzenesulfonamide VI and 136 mg (0.57 mmol) of 4-chloro-2-isocyanato-1,3-diisopropyl-benzene VIII in 10 mL of tetrahydrofuran. After stirring at room temperature for 3 hrs, the solvent was evaporated in vacuo. The residue was acidified with 2N HCl, then extracted with EtOAc. The EtOAc layer was dried over $Na_2SO_4$ and evaporated in vacuo. The residue was purified by column chromatography on silica gel eluting with $CH_2Cl_2$/MeOH::9/1 to give 190 mg of 1 (81%); mp 126–130° C.TLC:$CH_2Cl_2$/MeOH::9/1 single-spot material Rƒ 070.$^1$H-NMR (300 MHz DMSO-D$_6$) δ: (0.97, m, 12H), (2.76, m, 1H), (2.93, m, 1H), (3.10, m, 1H), (4.05, m, 1H), (7.04, s, 2H), (7.35, m, 1H), (7.50, m, 1 H), (7.77, m, 2H).

1-(1,2,3,5,6,7-Hexahydro-s-indacen-4-yl)-3-[2-fluoro-5-oxiranyl-benzenesulfonyl]-urea (2) (non-labeled)

Sodium hydride [60% dispersion in mineral oil, 30 mg (0.75 mmol)] was added to a solution of 148 mg (0.68 mmol) of 2-fluoro-5-oxiranyl-benzenesulfonamide VI and 150 mg (0.75 mmol) of 4-isocyanato-1,2,3,5,6,7-hexahydro-s-indacene X. After stirring at room temperature for 12 hrs, the solvent was evaporated in vacuo. The residue was acidified with 2N HCl, then extracted with EtOAc. The EtOAc layer was dried over $Na_2SO_4$ and evaporated in vacuo. The residue was triturated with hexane and filtered to give 210 mg of 2 (75%); mp 97–102° C.TLC:$CH_2Cl_2$/MeOH::9/1 single-spot material Rƒ 0.65.$^1$H-NMR (300 MHz DMSO-D$_6$) δ: (1.96, m, 4H), (2.47, m, 4H), (2.74, m, 5H), (3.11, m, 1H), (4.06, m, 1H), (6.90, s, 1H), (7.49, t, 1H), (7.61, m, 1H), (7.78, dd, 1H), (8.05, s, 1H).

[$^{14}$C]4-Chloro-2-isocyanto-1,3-diisopropyl-benzene VII

4-Chloro-2,6-diisopropyl-phenylamine VII hydrochloride (0.045 g, 0.18 mmol, 2 eq) was dispersed in ether, and triethylamine (57 mL, 0.41 mmol, 4.5 eq) was added. The solution was filtered through a cotton plug, and most of the ether evaporated in vacuo. The residual clear colorless oil was taken up in dry toluene (3 mL) and fitted to a vacuum manifold. The solution was degassed, cooled in a liquid nitrogen bath and evacuated. An ampoule containing [$^{14}$C] phosgene gas (5 mCi at 55 mCi/mmol) was fitted to the manifold, and the system evacuated. The manifold was then isolated from the pump, the ampoule broken, and the [$^{14}$C] phosgene allowed to vacuum transfer into the cooled reaction vessel. After 20 minutes, the cold bath was removed, and the reaction mixture warmed to room temperature. It was then backflushed with nitrogen and heated to 80° C. for one hour, after which time, no starting material remained (radio-TLC). The mixture was cooled to room temperature, and concentrated in vacuo. The yellow oil was filtered through a small plug of silica gel (hexanes) to give 5 mCi of [$^{14}$C]5-chloro-2-isocyanto-1,3-diisopropylbenzene VII, >99% radiochemically pure by radio-TLC (hexanes).

[$^{14}$C]4-isocyanto-1,2,3,5,6,7-hexahydro-s-indacene X

[$^{14}$C]Phosgene (35 mCi at 57 mCi/mmol) as a solution in toluene (35 mL) was cooled to 0° C., and triethylamine (0.50 mL, 3.6 mmol, 6 eq) and 1,2,3,5,6,7-hexahydro-5-indacen-4-ylamine IX (0.17 g, 0.1 mmol, 1.6 eq) were added as a solution in toluene (2 mL). After 15 minutes, the reaction was removed from the ice bath and let warm to room temperature over 30 minutes after which time radio-TLC analysis indicated desired product was present in 93%. The reaction mixture was concentrated in vacuo, and filtered through a plug of silica gel (hexanes). Significant white radioactive solid formed which did not dissolve in the hexanes. Concentration of the filtrate gave 9 mCi of [$^{14}$C] 4-isocyanto-1,2,3,5,6,7-hexahydro-5-indacene X, which was >99% pure by radio-TLC (hexanes).

[$^{14}$C]-1-(4-Chloro-2,6-diisopropyl-phenyl)-3-[2-fluoro-5-oxiranylbenzenesulfonyl]-urea (1)

The [$^{14}$C]5-chloro-2-isocyanto-1,3-diisopropylbenzene VIII (1.08 mCi at 55 mCi/mmol) and 2-fluoro-5-oxiranylbenzenesulfonamide VI (95 mg, 0.022 mmol, 1.1 eq) were dissolved in freshly distilled tetrahydrofuran and sodium hydride (2 mg) was added. After 5 minutes, radio-TLC indicated complete reaction. The reaction mixture was concentrated in vacuo, dissolved in water (5 mL) and extracted with ether. The aqueous was then acidified with 2N HCl, and extracted with ethyl acetate. The combined ethyl acetate layers were dried, filtered, concentrated and the residue chromatographed (silica gel, EtOAc) to give 0.84 mCi [$^{14}$C]Compound 1 (>99% pure radio-TLC, EtOAc).

[$^{14}$C]-1-(1,2,3,5,6,7-Hexahydro-s-indacen-4-yl)-3-[2-fluoro-5-oxiranylbenzenesulfonyl]-urea (2)

[$^{14}$C]4-Isocyanto-1,2,3,5,6,7-hexahydro-5-indacene X (0.9 mCi at 57 mCi/mmol) was dissolved in tetrahydrofuran (5 mL), and 2-fluoro-5-oxiranylbenzenesulfonamide VI (4.2 mg, 0.19 mmol, 1.2 eq) was added, followed by sodium hydride (2 mg). After 15 minutes, no starting material remained by radio-TLC. The reaction mixture was concentrated in vacuo, and the residue was dispersed in 0.2 M HCl (5 mL) and extracted with ethyl acetate (3×5 mL). The combined organic layers were dried, filtered, concentrated and the residue chromatographed (EtOAc) to give 0.58 mCi [$^{14}$C]Compound 2 (>99% pure by radio-TLC, EtOAc).

IL-1β production assay—ELISA method. Human monocytes were isolated from heparinized blood collected from normal volunteers. 100 ml of blood was diluted with 20 ml of RPMI 1640 medium that contained 5% FBS, 25 mM Hepes, pH 7.3, 2 mM glutamine, and 1% penicillin/streptomycin (Maintenance Medium). 30 ml of this suspension then was layered onto 15 ml of Lymphocyte Separation Medium (Organo Technicon) and centrifuged for 30 min at 1400 rpm at room temperature in a clinical centrifuge. The resulting mononuclear cell layer was harvested, diluted with Maintenance Medium, and the cells were pelleted by centrifugation. The recovered cells were washed with Maintenance Medium by repeated centrifugation. Each well of a 96 well plate was seeded with 2×10$^5$ mononuclear cells in 0.1 ml of Maintenance Medium; monocytes were allowed to adhere for 2 hr, then the medium (containing non-adherent cells) was replaced with 0.1 ml of fresh medium, and the monocytes were incubated overnight at 37° C. Monocytes were activated with 10 ng/ml of LPS (*E. coli*; serotype 055:B5) for 2 hr after which the medium was replaced with 0.1 ml of RPMI 1640, 20 mM Hepes, pH 6.9, 100 units/ml penicillin, 100 μg/ml streptomycin, 1% FBS (Release Medium) containing the indicated concentration of test agent; compounds were dissolved in DMSO and the final DMSO concentration in all wells was maintained at 0.2%. After a 15-min incubation, 2 mM ATP was introduced into each well (11 μl of 20 mM ATP previously adjusted to pH 7) and the cultures were incubated for an additional 3 hr at 37° C. Cells subsequently were removed by centrifugation, media supernatants were harvested, and IL-1β levels within the media samples were determined with a specific ELISA kit (R and D Systems); each data point is the average of quadruplicate determinations.

To prepare monocyte conditioned medium, mononuclear cells from 200 ml of blood were harvested by the Lymphocyte Separation Medium protocol described above and suspended in 40 ml of a Serum Free Medium (Gibco) designed for macrophage culture. Each of four 10 cm dishes was seeded with 10 ml of the mononuclear cell suspension and the cultures were incubated 2 hr at 37° C. to allow monocyte attachment. Media containing non-attached lymphocytes were discarded and 10 ml of fresh serum free medium containing 100 ng/ml of macrophage-colony stimulating factor was added to each dish. Monocytes were incubated overnight at 37° C. after which the media were replaced with 7.5 ml of RPMI 1640 medium containing 25 mM Hepes, pH 6.9, 1% FBS, and 10 ng/ml LPS. After a 3-hr incubation, Compound 3 was introduced into the media of some cultures to achieve a final concentration of 1 pM; the DASU was prepared as a concentrated stock solution in dimethylsulfoxide and added to the media such that the final dimethylsulfoxide concentration in all cultures was maintained at 0.2%. At this point, ATP was introduced to achieve a final concentration of 2 mM and the cultures were incubated for an additional 3 hr at 37° C. Media then were harvested, clarified by centrifugation, and utilized for determination of cytokine levels using cytokine-specific ELISA kits (R and D Systems).

IL-1β production assay—metabolic method. Human mononuclear cells were seeded (1×10$^7$ cells/well) into 6-well cluster dishes in 2 ml of RPMI 1640 medium containing 5% fetal bovine serum and 25 mM Hepes, pH 7.3. Monocytes were allowed to adhere for 2 hr after which the supernatants were discarded and the attached cells were rinsed once with 2 ml of Maintenance medium. The attached monocytes were incubated overnight at 37° C. in a 5% CO$_2$ environment. Cells were activated with LPS (10 ng/ml) for 2 hr, then labeled for 60 min in 1 ml of methionine-free RPMI 1640 medium containing 1% dialyzed fetal bovine serum, 25 mM Hepes, pH 7.2, and 83 μCi/ml of [$^{35}$S] methionine (Amersham Corp. Malvern PA. 1000 Ci/mmol). The labeled cells were rinsed with 2 ml Release Medium, after which 1 ml of Release Medium containing test agent was added and the cells were incubated for 15 to 60 min at 37° C. At this point fresh Release Medium containing 2 mM ATP (in the absence or presence of the test agent) was added to initiate cytokine posttranslational processing.

Cells and media were separated after 3 hr of stimulus-induced processing and the media were clarified by centrifugation to remove cells and/or cell debris; the resulting supernatants were harvested and adjusted to 1% in Triton X-100, 0.1 mM PMSF, 1 mM iodoacetic acid, 1 μg/ml pepstatin, and 1 μg/ml leupeptin by addition of concentrated stock solutions of these reagents. Adherent monocytes were solubilized by addition of 1 ml of an extraction buffer composed of 25 mM Hepes, pH 7, 1% Triton X-100, 150 mM NaCl, 0.1 mM PMSF, 1 mM iodoacetic acid, 1 μg/ml pepstatin, 1 μg/ml leupeptin, and 1 mg/ml ovalbumin; 50 μl of this extraction buffer also was added to the pellets obtained after clarification of the media supernatants and these samples were combined with the corresponding cell extract. After a 30 min incubation on ice, both the media and cell extracts were clarified by centrifugation at 45,000 rpm for 30 min in a Beckman table top ultracentrifuge using a TLA 45 rotor (Beckman Instruments, Palo Alto, Calif.).

IL-1β was immunoprecipitated from detergent extracts of cell and media samples by addition of 3 μl of a rabbit anti-human IL-1β serum (Collaborative Biochemical Products Bedford, Mass.). After a 2-hr incubation at 4° C., 0.25 ml of a 10% suspension of Protein A-Sepharose (Sigma) was added to each tube and the resulting immune complexes were recovered by centrifugation. The bead-bound complexes were washed 5 times with 10 mM Tris, pH 8, 10 mM EDTA, 1% Triton X-100, 0.4% deoxycholate, 0.1% SDS and once with 50 mM Tris, pH 6.8. The final pellets were suspended in 0.1 ml of disaggregation buffer and boiled for 3 min; beads were removed by centrifugation and the disaggregated immunoprecipitate supernatants were stored at −20° C. prior to analysis by SDS gel electrophoresis and autoradiography. Gels were soaked in Amplify (Amersham) prior to drying. Quantitation of the amount of radioactivity associated with the various species of IL-1β was determined with the use of an Ambis Image Analysis System (San Diego, Calif.) or by phosphorimager analysis.

Murine macrophages isolated by peritoneal lavage of Balb/c mice were seeded into 6 well dishes (precoated with Natrix); $1 \times 10^6$ cells were added per well in 2 ml of RPMI 1640 medium containing 5% FBS. After an overnight incubation, these cells were stimulated with LPS (1 μg/ml for 75 min) and then labeled for 60 min with [$^{35}$S] methionine (80 μCi) in 1 ml of methionine-free minimal essential medium containing 25 mM Hepes, 1 μg/ml LPS, and 1% dialyzed FBS. Labeled cells were washed with RPMI 1640, 25 mM Hepes, pH 7.3, containing 1 μg/ml LPS and 1% FBS after which 1 ml of the same medium containing allogeneic cytotoxic T lymphocytes was introduced in the absence or presence of Compound 3; a lymphocyte to macrophage ratio of 20 to 1 was employed. The cytolytic T lymphocyte preparation was prepared in advance by establishing an in vitro mixed lymphocyte reaction between C57/Bl mice effector spleen cells stimulated with irradiated target spleen cells obtained from Balb/c mice as detailed previously (Perregaux et al. *J. Immunol.* 157:57–64 (1996)). After 4 hr of co-culture the media were harvested and cleared of cells and/or cell debris by centrifugation, and released IL-1β was recovered by immunoprecipitation as detailed above. Immunoprecipitates were analyzed by SDS gel electrophoresis and the quantity of radioactivity associated with the 17 kDa IL-1β species was determined by Ambis Image analysis.

Identification of DASU binding proteins. Human monocytes (isolated as described above and plated on 6 cm dishes) were treated with [$^{14}$C]Compound 1 in 3 ml of Release Medium (devoid of FBS) for 60 min after which cells were washed twice with 5 ml of Release Medium containing 5% FBS and suspended in 1 ml of 25 mM Hepes, pH 7, 150 mM NaCl, 1 μg/ml pepstatin, 1 μg/ml leupeptin, containing 0.5% saponin. Lysates were clarified by ultracentrifugation and the recovered soluble fractions were exchanged into 10 mM Tris, pH 8, containing 1 μg/ml each of pepstatin and leupeptin with the use of Centricon 30 concentration units. Final concentrates were lyophilized and then solubilized in SDS sample buffer.

For purification of the DASU binding proteins, $4 \times 10^9$ THP-1 cells were incubated with 10 μM [$^{14}$C]Compound 1 in 100 ml of a hypotonic medium (27 mM NaCl, 0.9 mM $CaCl_2$, 0.5 mM $MgCl_2$, 0.53 mM KCl, 0.29 mM $KH_2PO_4$, 20 mM Hepes, pH 7, 5 mM glucose, 5 mM $NaHCO_3$, 10 ng/ml LPS) as a suspension culture for 60 min at 37° C., after which cells were harvested by centrifugation, washed with PBS, and suspended in 50 ml of 25 mM Hepes, pH 7, 30 mM KCl, 30 mM sodium gluconate, 0.9 mM $CaCl_2$, 0.5 mM $MgCl_2$, 1 μg/ml leupeptin, 1 μg/ml pepstatin. This cell suspension was disrupted by $N_2$ cavitation (650 psi for 15 min) and the resulting lysate was clarified by ultracentrifugation. The supernatant was applied to a 10 ml HiTrap Q column (Pharmacia; column assembled by placing two 5 ml HiTrap Q columns in series) equilibrated in 20 mM Tris, pH 8, 20 mM NaCl, 1 mM $MgCl_2$, 1 mM KCl, 1 μg/ml pepstatin, and 1 μg/ml leupeptin, and the column was eluted with a linear 200 ml gradient from 20 to 250 mM NaCl. Aliquots of each fraction were monitored by liquid scintillation counting and peak fractions were pooled. Samples of the individual peaks were disaggregated with SDS sample buffer and analyzed by PAGE and autoradiography.

Sequence analysis. Following tryptic digestion of protein samples isolated as Coomassie Blue-staining bands on SDS-PAGE, tryptic digests were fractionated by reversed-phase HPLC performed using a Hewlett-Packard 1090 chromatograph. Typically, a Vydac column type 218TP52 (2.1 mm×25 cm) was employed using a flow rate of 0.2 ml/min with the following solvents: solvent A, 0.1% trifluoroacetic acid in water; solvent B, 0.085% trifluoroacetic acid in acetonitrile. Major principles of the method used were as described (Rosenfeld et al. *Anal. Biochem.* 203:173–179 (1992); Fernandez et al. *Anal. Biochem.* 218:112–117 (1994)). Minor variations in the flow rate and type of column employed were made on occasion. Peaks detected by absorption at 220 nm were hand collected, reduced in volume if necessary by centrifugal concentration in a Speed-Vac (Savant Instruments), and in microfuge tubes subjected to amino acid analysis by automated Edman degradtion and HPLC using a Perkin-Elmer Applied Biosystems Procise 494A protein sequencing system. The resulting data were inspected and interpreted using Model 610 software (Perkin-Elmer Applied Biosystems).

Cloning and expression of DBP-31 and DBP-32. To clone cDNA encoding DBP-31, the sequence from accession #N46067 was employed to design sense and antisense primers. The sense primer (5'-AGGATCCACGATGTCCGGGGAGTCAG-3') (SEQ. ID. NO. 5) contained a BamHl site and the antisense primer (5'-CGAATTCAGAGCCCATAGTCACAG-3') (SEQ. ID. NO. 6) contained an EcoRI site for insertion into the pGEX2T expression vector (Pharmacia, Piscataway, N.J.). PCR reactions were performed for 14 cycles (94° C. for 20 sec, 65° C. for 20 sec, and 72° C. for 60 sec). The resulting double-stranded DNA products were analyzed by agarose gel electrophoresis. Fragments of the expected size were excised from agarose gel with a QlAquick gel extraction kit (Qiagen Venlo, NL), ligated into a pGEMT cloning vector (Promega, Madison, Wis.), and transformed into competent *E. coli* DH5α subcloning efficiency cells (Gibco BRL Grand Isle, N.Y.). After overnight growth on LB plates containing 100 μg/ml ampicilin, 0.5 mM isopropyl-β-D-thiogalactopyranoside and 40 μg/ml Xgal white colonies were selected and expanded by growth in liquid cultures. Plasmid DNA recovered from these cultures was digested with BamHl and EcoRl and the resulting restriction fragments were analyzed by agarose gel electrophoresis. Plasmids containing the correctly sized insert (740 bp) were analyzed by DNA sequence analysis.

For expression, DBP-31 DNA was cloned into the bacterial expression vector pGEX2T (Pharmacia Piscataway, N.J.) at the BamHl/EcoRl sites and *E. coli* DH5α cells again were transformed and plated on LB plates containing 100 μg/ml ampicilin. Positive colonies (confirmed by restriction enzyme digestion) were selected and plasmid DNA was isolated with a QlAquick kit. BL21 [DE3] cells (Novagen Madison Wis.) then were transformed with the plasmid DNA and grown on LB plates containing 100 μg/ml ampicilin. Single colonies were selected and inoculated into 100 ml of LB medium containing 50 μg/mi ampicilin, and these cultures were grown overnight at 37° C. with shaking (225 rpm). A 1 to 10 dilution of the seed cultures with fresh LB medium then was prepared, and the scale-up cultures were maintained at 37° C. with shaking (225 rpm) until the $OD_{600}$ reached a value of 0.4–0.6 (approximately 1 to 1.5 h). To induce synthesis of the fusion protein, 50 μM isopropyl-α-D-thiogalactopyranoside then was introduced and the cultures were incubated for an additional 2 hr at 37° C. Cells then were harvested by centrifugation and the resulting cell pellets were frozen at −20° C.

Primers used for the cloning of DBP-32 were designed based on the neucleotide sequence of the human EST accession #X87689. Both the forward (5'-TACGGATCCATGGCTGAAGAACAACCGC-3') SEQUENCE ID. NO: 7) and the reverse (5'-GTAGGATCCTTATTTGAGGGCCTTTGCCAC-3') (SEQUENCE ID NO: 8) primers were designed to contain BamHl sites. Cloning and expression were performed similar to the protocols employed above for DBP-31.

Frozen DBP-32 expressing cell pellets (8.2 gm of cell paste from 2 liters of culture) were suspended in 25 ml of a lysis buffer composed of 20 mM Tris, pH 8, 0.1% Triton X-100, 5 mM DTT, 1 mM phenylmethylsulfonylfluoride, 1 mM EDTA, 25 μg/ml leupeptin, 1 μg/ml pepstatin and 5 μg/ml aprotinin. Lysozyme was added to achieve a final concentration of 1 mg/ml and the suspension was incubated on ice for 30 min. At this point, $MgCl_2$ was added to achieve a final concentration of 10 mM and DNase (10 μg/g of cell paste) was introduced; the suspensions were incubated for 30 min on ice. The suspension was sonicated (40% duty/power 4), 3 to 4 times at 30–45 sec intervals. Cell extracts then were clarified by centrifugation (1 8,000×g for 30 min) and the supernatants were recovered. GST-DBP-32 was recovered from the soluble extract by application of 14 ml of this preparation to a 1 ml column of Glutathione Sepharose (sample applied at 0.5 ml/min). After application of the extract, the column was washed with 14 ml of phosphate buffered saline at 1 ml/min. Bound GST-fusion protein was then eluted by applying 0.1 M Tris HCl, pH 8, containing 20 mM glutathione; individual 1 ml fractions were collected and monitored for protein by measuring the $OD_{280}$. Peak fractions were pooled and desalted on an 8 ml Fast Desalting Column HR 10/10 (Pharmacia Piscataway N.J.) equilibrated with phosphate buffered saline. Buffer exchanged protein fractions were pooled and dithiothreitol was added to achieve a final concentration of 5 mM.

The GST-DBP-32 fusion protein was treated with a 1/200 ratio (on a μg basis) of thrombin for 2.5 hr at 25° C. after which the digest was applied to a MonoQ HR10/10 column (Pharmacia) equilibrated in 20 mM Tris, pH 8; sample was loaded on to the column at a rate of 4 ml/hr after which the column was washed for 10 min with 20 mM Tris, pH 8. A gradient from 0 to 30% 1 M NaCl in 20 mM Tris, pH 8 was applied for 30 min to elute the DBP-32 fragment; peak fractions were pooled and adjusted to 5 mM dithiothreitol. As a final purification step, the DBP-32 preparation was passed back over a small column of Glutathione Sepharose; the flow-through was collected and pooled to yield 98% pure DBP-32.

DBP-31 was purified by a similar procedure except that the MonoQ anion exchange chromatography step was omitted. Electrospray mass analysis of the purified products indicated that each of the two recombinant-derived polypeptides had the predicted mass. The amino termini of these products had short sequences derived from the thrombin-cleavable linker placed between GST and the DBP fusion partner; this was Gly-Ser in the case of DBP-32 and Gly-Ser-Thr in the case of DBP-31.

Labeling rDBPs. To demonstrate the predicted capacity of rDNA-derived DBPs to be radiolabeled by [$^{14}$C]Compound 2, samples of purified DBPs or bacterial GST (1 μg) were diluted into 20 μl of 25 mM Hepes, pH 7.3, 30 mM KCl, 30 mM sodium gluconate, 0.9 mM $CaCl_2$, 0.5 mM $MgCl_2$ and 1 mM DTT containing [$^{14}$C]Compound 2. After a 60-min treatment at 37° C., 4 μl of a 6-fold concentrated Laemmli sample buffer (Laemmli, U. K. *Nature* 227:680–685 (1970)) were added and the samples were heated at 56° C. for 5 min. Disaggregated samples were separated on 12% polyacrylamide mini Gels (Novex), after which the dried gels were analyzed by phosphorimager analysis. Competition experiments were conducted at 4° C. for 30 min in the same labeling format.

In vivo IL-1β production assay. Mice were given an i.p. injection of 1,pg of LPS in 0.5 ml of PBS. One hr later Compound 3 was dosed orally in 0.5% methylcellulose. After a further one hr, an i.p. injection of ATP, disodium salt (30 mM) in 0.5 ml of PBS, was administered; the pH of the ATP solution was adjusted to 7.3 prior to injection. Fifteen minutes later, the mice were killed by cervical dislocation and the peritoneal cavity lavaged with 3 ml of ice cold PBS containing 10 units/ml of heparin sodium salt, 0.25 mM phenylmethysulfonyl fluoride, 1 μg/ml leupeptin, 1 μg/ml pepstatin, and 1 mM EDTA. IL-1α and IL-1β in the lavage fluid were measured using commercially available ELISA kits from Endogen (IL-1α) and Genzyme (IL-1β).

What is claimed is:

1. A method of screening for the ability of a compound to inhibit the production of an inflammatory cytokine comprising determining the ability of sad compound to bind to a polypeptide encoded for by the polynucleotide sequence of SEQUENCE ID NO: 1, or to a polypeptide encoded for by a polynucleotide sequence having 95% homology to SEQUENCE ID NO: 1 and assaying for inhibition of said inflammatory cytokine.

2. A method as recited in claim 1, wherein the inflammatory cytokine is IL-1 or IL-18.

3. A method of screening for the ability of a compound to inhibit the production of an inflammatory cytokine comprising determining the ability of said compound to bind to a polypeptide encoded for by the polynucleotide sequence of SEQUENCE ID NO: 2, or to a polypeptide encoded for by a polynucleotide sequence having 95% homology to SEQUENCE ID NO: 2 and assaying for inhibition of said inflammatory cytokine.

4. A method as recited in claim 3, wherein said inflammatory cytokine is IL-1 or IL-18.

5. A method of screening for the ability of a compound to inhibit the production of an inflammatory cytokine comprising determining the ability of said compound to bind to a polypeptide having the amino acid sequence of SEQUENCE ID NO: 3, or to a polypeptide sequence having 95% homology to SEQUENCE ID NO: 3 and assaying for inhibition of said inflammatory cytokine.

6. A method as recited in claim 5, wherein said inflammatory cytokine is IL-1 or IL-18.

7. A method of screening for the ability of a compound to inhibit the production of an inflammatory cytokine comprising determine the ability of said compound to bind to a polypeptide having the amino acid of SEQUENCE ID NO: 4, or to a polypeptide sequence having 95% homology to SEQUENCE ID NO: 4 and assaying for inhibition of said inflammatory cytokine.

8. A method as recited in claim 7, wherein said inflammatory cytokine is IL-1 or IL-18.

9. A method of screening for the ability of a compound to inhibit the production of an inflammatory cytokine comprising determining the ability of said compound to bind to a polypeptide encoded for by the polynucleotide sequence of SEQUENCE ID NO: 1, or to a polypeptide encoded for by a polynucleotide sequence having greater than 95% homology to SEQUENCE ID NO: 1 and assaying for inhibition of said inflammatory cytokine.

10. A method as recited in claim 9, wherein said cytokine comprises IL-1 or IL-18.

11. A method as recited in claim 9, said method further comprising the screening of a polypeptide having greater than 95% homology to the polypeptide encoded for by SEQUENCE ID NO: 1.

12. A method of screening for the ability of a compound to inhibit the production of an inflammatory cytokine comprising determining the ability of said compound to bind to a polypeptide encoded for by the polynucleotide sequence of SEQUENCE ID NO: 2, or to a polypeptide encoded for by a polynucleotide sequence having greater than 95% homology to SEQUENCE ID NO: 2 and assaying for inhibition of said inflammatory cytokine.

13. A method as recited in claim 12, wherein said cytokine comprises IL-1 or IL-18.

14. A method as recited in claim 12, said method for comprising the screening of a polypeptide having greater than 95% homology to the polypeptide encoded for by SEQUENCE ID NO: 2.

15. A method of screening for the ability of a compound to inhibit the production of an inflammatory cytokine, including IL-1 or IL-18, comprising the ability of said compound to bind to a polypeptide having an amino acid sequence of SEQUENCE ID NO: 3, or to a polypeptide having greater than 95% homology to SEQUENCE ID NO: 3 and assaying for inhibition of said inflammatory cytokine.

16. A method as recited in claim 15, wherein said cytokine consists of IL-1.

17. A method as recited in claim 15, wherein said cytokine consists of IL-18.

18. A method of screening for the ability of a compound to inhibit the production of an inflammatory cytokine, including IL-1 or IL-18, comprising the ability of said compound to bind to a polypeptide having an amino acid sequence of SEQUENCE ID NO: 4, or to a polypeptide havinggreater than 95% homology to SEQUENCE ID NO: 4 and assaying for inhibition of said inflammatory cytokin.

19. A method as recited in claim 18, herein said cytokine consists of IL-1.

20. A method as rejected in claim 18 wherein said cytokine consists of IL-18.

21. A method of screening for the ability of a compound to inhibit the production of the cytokine, IL-1 or IL-18, comprising determining the ability of said compound to bind to a polypeptide encoded for by the polynucleotide sequence of SEQUENCE ID NO: 1, or to a polypeptide encoded for by a polynucleotide sequence having greater than 95% homology to SEQUENCE ID NO: 1 and assaying for IL-1 or IL-18 respectively.

22. A method of screening for the ability of a compound to inhibit the production of the cytokine, IL-1 or IL-18, comprising determining the ability of said compound to bind to a polypeptide encoded for by the polynucleotide sequence of SEQUENCE ID NO: 2, or to a polypeptide encoded for by a polynucleotide sequence having greater than 95% homology to SEQUENCE ID NO: 2 and assaying for IL-1 or IL-18 respectively.

23. A method of screening for the ability of a compound to inhibit the production of the cytokine, IL-1 or IL-18, comprising determining the ability of said compound to bind to a polypeptide having an amino acid sequence of SEQUENCE ID NO: 3 and assaying for IL-1 or IL-18 respectively.

24. A method of screening for the ability of a compound to inhibit the production of the cytokine, IL-1 or IL-18, comprising determining the ability of said compound to bind to a polypeptide having an amino acid sequence of SEQUENCE ID NO: 4 and assaying for IL-1 or IL-18 respectively.

* * * * *